United States Patent
Blackman et al.

[11] Patent Number: 5,919,679
[45] Date of Patent: Jul. 6, 1999

[54] METHOD AND APPARATUS FOR ALTERING IONIC INTERACTIONS WITH MAGNETIC FIELDS

[75] Inventors: Carl F. Blackman, Raliegh, N.C.; Janie P. Blanchard, Oakland, Calif.

[73] Assignee: The United States of America as represented by the Environmental Protection Agency, Washington, D.C.

[21] Appl. No.: 08/896,627

[22] Filed: Jul. 18, 1997

Related U.S. Application Data

[63] Continuation-in-part of application No. 08/329,980, Oct. 27, 1994, abandoned, and a continuation-in-part of application No. 08/466,437, Jun. 6, 1995, abandoned.

[51] Int. Cl.[6] .................................................... C12N 13/00
[52] U.S. Cl. ........................ 435/173.1; 435/173.2; 435/173.8
[58] Field of Search .............................. 435/173.1, 173.2, 435/173.8; 422/82.01

[56] References Cited

U.S. PATENT DOCUMENTS

| | | | |
|---|---|---|---|
| 5,045,050 | 9/1991 | Liboff et al. | 600/9 |
| 5,087,336 | 2/1992 | Liboff et al. | 204/155 |

*Primary Examiner*—Jon P. Weber
*Attorney, Agent, or Firm*—Browdy and Neimark

[57] ABSTRACT

A method is presented for altering or affecting ionic interactions in systems containing an unhydrated ion, including cells and organisms, using magnetic fields. The method involves controlling the orientation and varying the intensity and fluctuation frequency of paired static and sinusoidally varying magnetic fields in such a way as to create certain magnetic interactions between ions and the molecules with which they are associated. Using the ion parametric resonance (IPR) model developed in the present invention, the magnetic fields can be adjusted to control precisely the desired orientation, intensity and fluctuation frequency of the magnetic fields.

13 Claims, 8 Drawing Sheets

METHOD AND APPARATUS FOR ALTERING IONIC INTERACTIONS WITH MAGNETIC FIELDS

CROSS REFERENCE TO RELATED APPLICATIONS

The present application is a continuation in part of Ser. No. 08/329,980, filed Oct. 27, 1994, now abandoned, and Ser. No. 08/466,437, filed Jun. 6, 1995, now abandoned, the entire contents of both of which are hereby incorporated by reference.

FIELD OF THE INVENTION

The present invention is directed to a method for using magnetic fields to alter behavior of ions.

Background of the Invention

Tissue and cell development have been studied extensively to determine the mechanisms by which maturation, maintenance and repair occur in living organisms. Generally, development of a cell or tissue can be considered as a transformation from one state or stage to another relatively permanent state or condition. Development encompasses a wide variety of patterns, all of which are characterized by progressive and systematic transformation of the cells or tissue.

In many instances it is desirable to control or alter the development of cells and tissue in vivo. It is hoped that means can be provided to restore or maintain the natural order of an organism after a debilitating injury, disease or other abnormality.

As will be appreciated by those skilled in the art, tissue and organic development involve complex processes of cellular growth, differentiation and interaction mediated by complex biochemical reactions. At the genetic level, development is regulated by genomic expression; at the cellular level, the role of membrane interaction with the complex biochemical milieux of higher organisms is instrumental in development processes. Moreover, remodeling of tissues or organs is often an essential step in the natural development of higher organisms.

A role for biologically active ions in cellular activity is well established. In Liboff et al., U.S. Pat. No. 4,818,697, techniques are disclosed for controlling the movement of a preselected ionic species across the membrane of a living cell. The inventors disclose that by exposing a region of living tissue of a subject such as a human or animal to an oscillating magnetic field of predetermined flux density and frequency, the rate of tissue growth can be controlled. For stimulating bone growth rate, a fluctuating magnetic field is tuned to the specific cyclotron resonance frequency of a preselected ion such as $Ca^{++}$ or $Mg^{++}$. Additionally, Liboff et al., in U.S. Pat. No. 4,932,951, disclose the use of cyclotron resonance tuning to control the growth rate of non-osseous, non-cartiliginous connective solid tissue. In U.S. Pat. No. 5,067,940, Liboff et al. disclose a method and apparatus based on cyclotron resonance tuning which allow the growth rate of cartilaginous tissue to be regulated. An even more important use of cyclotron resonance tuning which is of particular significance in the treatment of elderly patients is disclosed in Liboff et al. U.S. Pat. No. 5,100,373, which deals with a method and apparatus for treating and preventing osteoporosis, both locally and systemically. Additional patents granted to Liboff and his co-workers in the field of ion cyclotron resonance include U.S. Pat. Nos. 4,818,697; 4,932,951; 5,045,050; 5,059,298; 5,067,940; 5,077,943; 5,087,336; 5,088,976; 5,100,373; 5,106,361; 5,123,898; 5,143,588; 5,160,591, and 5,193,456. All of the above-cited patents are hereby incorporated by reference in their entirety. These patents address various applications of the concept of field induced changes in ion transport in biological systems. The primary requirement for these applications is for a time varying (AC, preferably sinusoidal) magnetic field and a static magnetic field oriented parallel to the AC field. Liboff postulates, without explicit theoretical support, that the maximum influence will occur when $B_{ac}=B_{dc}$. Furthermore, there is the requirement for specific frequencies of AC field to tune to resonance conditions for particular ions of interest.

The results of a number of studies suggest that low-intensity and low-frequency electric and magnetic fields may influence physiologic processes in biological systems. However, most theoretical models developed to date have been unable to establish a predictive association between low-intensity field exposure and biological results. Some models of electric and magnetic field interactions with biological systems, for example, have focused on endpoints associated with direct energy deposition into the system from the fields or from the induction of body currents, and suggest that a single variable, such as AC field intensity, is responsible for the observed results. Partially as a result of these incomplete models, many experimental reports fail to document all relevant field exposure parameters and do not establish a clear protocol for obtaining repeatable results. Inconsistencies between experimental results have subsequently been interpreted by some as evidence that electric or magnetic fields may not be the causal factors (e.g., Adair, 1991; 1992). While there is much theoretical support for resolving AC and DC fields into parallel and perpendicular components in order to determine how they will affect biological systems, experimental efforts often fail to document the relative orientation between the AC and DC fields. In other experiments, different field variables such as frequency, temporal duration of fields, and relative alignment with the local geomagnetic field have been characterized on an ad hoc basis without clear guidance from a theoretical model to indicate which parameters were critical (Adey, 1992; Blackman et al., 1985, 1988, 1990; Blackman, 1992; Liboff, 1985, 1992; Liboff et al., 1987; Smith et al., 1987; Thomas et al., 1986).

A variety of theoretical models have been developed to describe the interaction of different combinations of static (DC) and extremely-low-frequency time-varying (AC) magnetic fields with living systems. In fact, most theoretical works, including quantum mechanics texts (e.g. Yariv, 1982), focus exclusively on how an AC magnetic field oriented perpendicular to the DC magnetic field will alter the spin of an ion. Edmonds (1993), for example, recently developed a model that concentrated on the case of perpendicular AC and DC fields. Most of the above-described models are largely descriptive, without being predictive. The ion cyclotron resonance (ICR) model, originally formulated by Liboff (cf. Liboff, 1985, McLeod and Liboff, 1987) and discussed by Durney (1988), Halle (1988) and Sandweiss (1990), describes how unhydrated ions might have distinct resonance type responses caused by the local DC magnetic field.

The fundamental premise of the ICR model is that parallel magnetic fields tuned for calcium, or a limited set of other selected ions, enhance the passage of those ions across the plasma membrane of the cell, only when $B_{ac}=B_{dc}$.

Theoretical support for the plausibility of measurable biological effects occurring as a result of exposure to parallel DC and AC magnetic fields can be found in the work of Chiabrera and colleagues (Chiabrera and Bianco, 1991; Chiabrera et al., 1991, 1993; Bianco and Chiabrera, 1992). They applied their model to a variety of biologically active ions in addition to calcium using the charge to mass ratio for the unhydrated state, a condition that may exist in ion-ligand components of biological molecules. Chiabrera and colleagues suggested that ions affected by ICR model conditions might be located in binding sites formed by molecular crevices that would exclude hydration of the ions. Although the ICR model predicts enhanced responses by specific ions when the AC frequency corresponds with the ICR model conditions, which are different for each ion, it does not indicate how the response might vary with different AC flux densities. Thus, the ICR model does not anticipate the distinct response form subsequently predicted for increasing $B_{ac}$ at constant $B_{dc}$ and $f_{ac}$.

Lednev (1991) incorporated Liboff's model, in a limited sense, in his examination of how parallel AC and DC magnetic fields might influence ions bound in ligand structures specific to $Ca^{++}$.

The ion parametric resonance (IPR) model, originally disclosed in Ser. No. 08/329,980, differs from Lednev's model in three critical ways: it specifically includes a $(-1)^n$ term multiplying the Bessel function prediction, the IPR model Bessel function argument is twice that of the Lednev model, and the IPR model considers a wider range of candidate ions, through an expanded understanding of the role of the ion in creating a biologically significant change.

The IPR model considers the potential effects on any unhydrated ion, or any entity that behaves like an unhydrated ion, presumably bound within a molecular structure, that can influence the observed biological response. The molecular structure may be composed of proteins, nucleic acids, or lipids, either singly or in any combination, as long as the structure itself requires an ionic cofactor to function. Extension to unhydrated ions beyond $Ca^{++}$ can be inferred in part by the work of Liboff (1985, 1992) and Chiabrera and colleagues, op. cit.

DEFICIENCIES IN BACKGROUND ART

Although for a long time it has been postulated that magnetic fields have potential effects on biological systems, there has been no clear evidence to date indicating the critical parameters influencing the effects. As a result, replication of observed effects has been limited at best. Lacking clear indication of the possible causes and forms of magnetic field influence, a linearly increasing effect with increasing AC field strength was assumed. However, Liboff gives no guidance beyond a maximum at $B_{ac}=B_{dc}$ after which one must experiment unduly to obtain precise values of $B_{ac}$ and $B_{dc}$ that will be useful in treating a particular system. However, the present inventors have discovered that under the specific conditions identified herein, neither this assumption nor Liboff's postulated maximum effect when $B_{ac}=B_{dc}$ is correct.

The work by Liboff et al. (1987) describing the transport of calcium/magnesium ions across a membrane of cells and bones considers specifically the physical motion of those ions as a result of the application of magnetic fields whose effect is to transform the random motion of those ions to a path matching the geometric form of the spiral channel postulated to provide passage across the membrane. The frequency for these ions is only the same at the fundamental. However, Liboff does not predict the hydrogen trigger at calcium tuning.

Although the "characteristic resonance frequency" of the IPR model is identical in mathematical form to that of the ICR model resonance, it will be seen that resonance as defined for the IPR model of this application is the mathematical inverse of that defined for the ICR model. Further, the mechanism of interaction postulated for the IPR model is distinct from that of the ICR model by virtue of abandoning a geometric concept and focussing on the ion's role within a molecular structure, such as an enzyme, protein, nucleic acid, and that the IPR model's consideration of candidate ions is, therefore, broader than is that of the ICR model. Since $$n = \frac{q}{m} \frac{B_{dc}}{2af_{ac}}$$

at constant $B_{dc}$, a higher n requires a lower frequency.

Sandyk (1993) examined the application of magnetic fields to influence the pineal gland in patients with Parkinson's disease to moderate the melatonin caused hyperglycemia. However, the AC field flux densities applied were substantially below those postulated to be effective by the IPR model, assuming an approximate geomagnetic source of the ambient DC magnetic field. Further, three different orientations for the applied AC fields, with respect to a presumably fixed DC field, were required to produce an effect, obviating any requirement for parallel fields.

The work of Liburdy et al. (1993) also demonstrated the use of AC magnetic fields to control the influence of melatonin without a clear indication of the AC magnetic field orientation with respect to that of the ambient DC magnetic field. Lerchl et al. (1991) specifically considered the influence of parallel fields on pineal gland function, showing that a single selected combination of fields reduced the synthesis and production of melatonin. This single data point is between the maximal effect and null effect predictions by the IPR model, assuming $Ca^{++}$ resonance. Lerchl further considers the distinction between parallel and perpendicular fields, postulating them to follow a cosine law form, although this was not substantiated by any data. Although these works, taken together, appear to suggest a likely effect on either melatonin production, or its action in vivo, or both, they each give results for single combinations of applied magnetic fields without any further guidance for how these effects might change with variations in AC flux density, frequency, or DC flux density. As will be shown below, no person of ordinary skill in the art at the time of these publications would have been motivated to demonstrate the parallel AC and DC magnetic fields would be able to control precisely the function of melatonin, either applied or as produced by the pineal gland, in the controlled and distinctly predicted non-linear form predicted by the IPR model. Further, no person of ordinary skill in the art at the time of these publications would have been motivated to demonstrate the three distinct responses shown under parallel (on or off resonance) and perpendicular AC and DC magnetic fields, indicated by the present application, across a critical range of AC flux densities.

Absent from any of the aforementioned arts is any recognition of:

(a) the variation in critical influence of the strength (flux density) of the AC magnetic field on the magnitude of magnetic field influence on a biological system;

(b) the importance of reducing the static magnetic field perpendicular to the AC magnetic field to near zero value in order to distinctly get the IPR model predicted result;

(c) the role of AC frequency;

(d) the potential for a single exposure condition to differentially stimulate multiple ions concurrently;

(e) evidence of the unique role of a variety of otherwise biologically significant ions, including but not limited to hydrogen, sometimes critical, in a biological system's response to a magnetic field;

(f) the explicit recognition of peak AC field measurements (in contrast to rms) as the appropriate metric.

(g) a clearly prescriptive identification of how the system might differentially respond to variations in $B_{ac}$ (with $B_{dc}$ and $f_{ac}$ constant) except for a postulated effect when $B_{ac}=B_{dc}$ (with $B_{ac}$ interpreted by some experimenters as rms and by others as peak).

(h) indication of the distinction in biological/chemical system response between exposure to parallel and exposure to perpendicular AC and DC magnetic fields, and the critical importance of maintaining strictly parallel fields in order to get the distinct response form predicted by IPR model;

(i) the role of the DC field in selecting an ion or in increasing the off-resonance effect wherein the same AC field could either change $f_{ac}$ or $B_{dc}$ to make no effect.

It has also been found that the ion cyclotron resonance condition disclosed by Liboff is a special case of the ion parametric resonance model that is not extendable via harmonics, as Liboff and others have assumed to date.

In the IPR model of application Ser. No. 08/329,980, magnetic field interactions with ions are characterized by a frequency index, n, defined as the ratio of the (ion specific) cyclotron resonance frequency to the applied AC frequency. When n for a given ion has integer value, the system is said to be in resonance for that ion. When n=1, resonance is also found with Liboff's ICR model.

Theoretical models developed to date have been unable to establish a detailed predictive association between low-intensity field exposure and biological results. Some models of electric and magnetic field interactions with biological systems focus on endpoints associated with direct energy deposition into the system from the fields of induction of body currents and suggest that a single variable, such as AC field intensities, is responsible for the observed results. Partially as a result of these implicit models, many experimental responses fail to document all relevant field exposure parameters and do not establish a clear protocol for repeatable results. Inconsistencies between experimental results have subsequently been interpreted by some as evidence that electric or magnetic fields may not be the causal factors (cf. Adair, 1991, 1992).

Most experimental efforts heretofore have failed to document or consider the importance of the relative orientation between the AC and DC fields. In some experiments, different field variables such as frequency, temporal duration of fields, and relative alignment with the local geomagnetic field have been characterized on an ad hoc basis without clear guidance from a theoretical model to indicate which parameters were critical (Adey, 1975, 1988 a, b, 1992; Blackman et al., 1985, 1988, 1990; Blackman, 1992; Liboff, 1985, 1992; Liboff et al., 1987 b; Smith et al., 1987; Thomas et al., 1986).

SUMMARY OF THE INVENTION

It is an object of the present invention to overcome the aforesaid deficiencies in the prior art.

It is another object of the present invention to define all of the magnetic field exposure conditions that are required to produce effects in a chemical or biological system.

It is another object of the present invention to change a selected response of a chemical or biological system (including enzyme, cell, organ, or organism) containing at least one unhydrated ion that influences that selected response by creating a resonance for one or more of those ions having significance in the system, according to the precise definition for resonance given in the text below.

It is a further object of the present invention to provide an influence on a selected chemical or biological system which oscillates between maximal and no effect in a mathematically well-defined non-linear manner as a function of the AC magnetic flux density only when the system can be said to be at resonance for an ion which is significant to the particular system.

It is a further object of the present invention to provide a means for precisely controlling the degree of response of a biological or chemical system to an externally imposed condition.

It is a further object of the present invention to provide a means for precisely controlling the degree of response of a biological or chemical system to an externally imposed combination of AC and DC magnetic fields.

It is a further object of the present invention to provide a means for precisely controlling the degree of response of a biological or chemical system to an externally applied agent.

It is another object of the present invention to provide a means for changing the effects described above for specific combinations of AC and DC magnetic fields by reorienting the AC and DC magnetic fields with respect to each other.

It is a further object of the present invention to create three biological/chemical response options in a treated system for selected AC and DC magnetic field flux densities and AC frequency: (1) on-resonance parallel AC and DC magnetic fields (creating, for example, maximal inhibition of a biological response); (2) off-resonance parallel AC and DC magnetic fields (creating no change in the biological/chemical system in comparison to the unexposed case); and (3) on-resonance perpendicular AC and DC magnetic fields (creating, for example, maximal increases in the biological response).

The present invention provides a method for altering, controlling or affecting ionic interactions in systems containing an unhydrated ion, including cells and organisms, using magnetic fields. The method involves controlling the orientation and varying the intensity and fluctuation frequency of paired static and sinusoidally varying magnetic fields in such a way as to create certain magnetic interactions between ions and the molecules with which they are associated. Using the ion parametric resonance (IPR) model developed in the present invention, the magnetic fields can be adjusted to control precisely the desired orientation, intensity and fluctuation frequency of the magnetic fields to create the desired response in a chemical or biological system.

Essentially, the IPR model considers how an ion cofactor in a key molecular complex, such as an enzyme binding site, alters the conformation states of that molecular complex, resulting in an observable change in the biological or chemical system in which it is contained. In an ion-enzyme complex, the result is believed to be a change in reaction kinetics. The ionic influence is controlled by the restructuring of internal energy states of the molecular complex resulting from externally applied magnetic fields. The effectiveness of this restructuring in creating an observable biological change is in turn influenced by the resonance relationship between the frequency of the applied AC magnetic field, the flux density of the applied DC magnetic field, and the particular ion's charge to mass ratio, as well as by special features of ion-molecular interactions that allow resonance response to occur for a sufficient time to effect a change.

The desired parameters are calculated from a mathematical model developed to quantify the interactions of magnetic fields with ions and their associated molecules. The method which comprises the present invention is based upon using this mathematical model to define the magnetic fields to be used to achieve a particular effect on the system. By using this mathematical model, the present invention makes it possible to determine parameters necessary for causing specific ionic interactions and can accurately define the particular magnetic fields to create these effects. The invention, thus, can be used for non-destructive characterization and evaluation of chemical and biological systems, as well as for controlling conditions within chemical and biological systems, as well as for controlling conditions within chemical and biological systems.

The ion parametric resonance (IPR) mathematical model of the present invention examines ionic responses to parallel AC and DC magnetic fields and, by specifying the functional influences of all magnetic field parameters, provides detailed predictions of the expected atomic or ionic level responses that in turn influence observed biological or chemical endpoints.

According to the present invention, the influence of the strength (flux density) of an AC magnetic field oscillates between maximal and no effect as the AC field is increased, not in direct proportion to the magnitude of the AC field, but as a function of a Bessel function of the first kind whose argument involves the ratio of the frequency index (defined within) and the magnitudes of the AC and the DC magnetic fields. The static magnetic field that is perpendicular to the AC magnetic field must be reduced to near zero to avoid alternative interaction with the phenomena. The ratio between the AC frequency and the static magnetic field is used for the identification of multiple ions for which this effect occurs, and the multiple chemical systems differentially stimulated concurrently using a single exposure condition, as well as a crucial role for hydrogen ions, which had heretofore been unrecognized.

Thus, the present invention is directed to methods for affecting an unhydrated ion by subjecting that ion to a combination of AC and DC magnetic fields and applying a mathematical understanding of the parameters wherein the flux density and the AC frequency are selected. For purposes of the present invention, an "unhydrated ion" is one which has the properties of an unhydrated ion, irrespective of whether the ion is actually unhydrated in the system in question.

The present inventors have discovered the following with respect to affecting an unhydrated ion with a combination of an AC and a DC magnetic field:

(1) There is a critical influence of the strength (flux density) of the AC magnetic field on the magnitude of magnetic field influence on a system containing an unhydrated ion.

(2) There is the potential for a single exposure to a predetermined magnetic field to differentially stimulate multiple unhydrated ions simultaneously, each of which is predicted to have a unique response form given by the IPR model of the present invention.

(3) It is important to reduce the static magnetic field perpendicular to the AC magnetic field to near zero value in order to distinctly achieve the IPR model predicted result;

(4) The IPR model demonstrates the unique role of a variety of otherwise biologically significant ions.

(5) There is an explicit recognition of peak AC measurements (in contrast forms) as the appropriate measurement;

(6) a clearly prescriptive identification of how the system might differentially respond to variations in $B_{ac}$ (while $B_{dc}$ and $f_{ac}$ remain constant) except for a postulated effect when $B_{ac}=B_{dc}$ with $B_{ac}$ interpreted by some experimenters as rms and by others as peak.

(7) Indication of the distinction in the response of a biological or chemical system between exposure to parallel and exposure to perpendicular AC and DC magnetic fields.

(8) The critical importance of maintaining strictly parallel fields in order to obtain the distinct response form predicted by the IPR model, that is, parallel is on or off, while perpendicular is on.

(9) Hydrogen trigger ion's influence is stronger than any other ions which also may be at resonance, i.e., other ions are weaker than hydrogen. Hydrogen is seen over the influence of fields or other ions within a defined, determinable critical $B_{ac}/B_{dc}$ range. That is, there is no need to experiment.

According to the present invention, alternative forms of response by a chemical or biological system containing at least one unhydrated ion are produced by adjusting the relative amount of $B_{ac}$ perpendicular to $B_{dc}$. The addition of a perpendicular $B_{dc}$ can dramatically attenuate or even eliminate the response caused by parallel $B_{ac}$ and $B_{dc}$. Substituting a $B_{dc}$ perpendicular to the $B_{ac}$ at constant $B_{ac}$ in place of the parallel $B_{dc}$, called for in the IPR model situation, can cause a diminution or a reversal in the direction of the response in a chemical or biological system.

The present invention is particularly useful in the following fields:

(1) Diagnosis

Methods for determining which ions, and their oxidation states, are involved in chemical and biochemical complexes and reactions. The effect may be observed by using a direct physical method for detection, e.g, molecular conformation or molecular dynamics techniques, or indirect methods that look at reaction products or biological responses.

(2) Altered Reactions and Processes

Methods for altering and controlling ion associated chemical and biochemical complexes and reactions, including changes in the balance between alternative, competing chemical pathways that lead to a different mix of products. In addition, alterations may occur in any process that has an ion as part of a regulatory control mechanism, as in the case of ion gates in some protein channels in cell membranes.

(3) Changing Biological Processes

Methods for altering or controlling biochemical processes which change an organism's response to environmental agents or influences. Any process that involves ion interactions with biological molecules is potentially subject to control or alteration including such diverse actions from animal/human response to endogenous or exogenous chemicals, e.g., opioids, and to alterations in acquisition of learning and retention of memory.

(4) Deliver/Activation Processes

Methods for triggering chemical or biochemical reactions in localized regions of space. For example, biologically active compounds attached to carrier molecules or encased in vesicles designed with ionic cofactors may be released at particular sites in the body when the kinetic interactions of the particular ions with the carrier or vesicle are altered by appropriate exposure to magnetic fields. Alternatively, a drug or other agent may be delivered diffusely but a combination of magnetic fields as determined according to the present invention may then be focused on the desired site of interaction or to control the process. The biologically active compounds may include an active component complexed within an inactivating agent, which includes an ion cofactor. The compounds are then rendered active or inactive, as desired, when the ionic interaction is changed by appropriate magnetic field exposure conditions within a specific volume of space.

In other words, the IPR mathematical model of the present invention examines ionic responses in systems which contain an unhydrated ion to parallel AC and DC magnetic fields and, by specifying the functional influences of all magnetic field parameters, provides detailed predictions of the expected atomic and molecular level responses. Once these predicted responses are known, using the IPR model, combinations of magnetic fields can be applied to biological or chemical systems to achieve a desired result.

Although there is theoretical support for the idea that changes in ionic interactions with biological matrices lead to alterations in biological responses at the cellular level, specific details connecting observable quantities to effects on ions within a biological system remain uncertain. It is, however, well established that biological activity is driven by enzymatically controlled chemical reactions and that some enzymes incorporate specific ions as cofactors to initiate or modulate their reaction rates. The role of other specific ions can be seen in selective functions of proteins, such as those involved in electron or oxygen transport.

Ionic cofactors and reaction centers and their dynamic interactions driven by thermal motion are critical elements in biological activities. Native proteins at biologically relevant temperatures are not static forms but fluctuate constantly, passing through a variety of similar configurations due to thermal influence. Karplus and Petsko (1990) point out the importance of this kinetic view of proteins by stating, "it would not be surprising if internal motions had been subjected to selective pressure during evolution. Just as structure is selected on the basis of functions, there could be selection for certain internal motions, a consequence of the structure, if they had specific functional roles." Thus, thermally driven kinetic motion is an essential element of protein function, with functional selection of specific motions or forms evolving over time.

As an example of a selective form, some enzymes have ligand-bound ions that can impart stability and conformational changes necessary for reaction sites to orient for optimal enzymatic activity. The interaction of an ion with its ligands in a protein can be viewed as an oscillator with a characteristic set of vibration frequencies, or, alternatively, a characteristic set of energies. Changes in protein function or enzyme activity are presumably a function of various minor structural or conformational states assumed by the protein represented by changes in energy levels of the reaction sites. Thus, thermal energy in active biological systems is normally present to promote random transitions between protein energy levels.

Although it is not certain what the role of changes in ion energetics in ion-protein dynamics and on reaction site kinetics is, it is believed that hydrogen bonding holds ligands in place, relatively loosely. Once the hydrogen bonds are destabilized, i.e., by application of a particular magnetic field, the ligands more easily release the metal from the ligand. In the present invention, the IPR model permits one to control the ion binding and to calculate the values of magnetic fields to obtain the desired degree of response.

According to the present invention, the influence of the strength (flux density) of an AC magnetic field oscillates between maximal and no effect as the AC field is increased, not in direct proportion to the magnitude of the AC field, but as a function of a Bessel function of the first kind whose argument involves the ratio of the frequency index and the magnitudes of the AC and the DC magnetic fields.

It is well known that many biological and chemical systems have very similar processes, such as the storage and utilization of genetic information, response to environmental stimuli, utilization of nutrients, reproductive processes, etc. Moreover, much biological activity is driven by enzymatically controlled chemical reactions, and some enzymes incorporate specific ions as cofactors to initiate or modulate their reaction states. The role of other specific ions is evidenced in selective functions of protein, such as those involved in electron or oxygen transport.

Thus, the method of the present invention permits one to tune for specific ions or ion groups as determined by the effective bandwidth for ions with closely spaced frequency indices. Because of the possible bandwidth overlap, the model and the results obtained make the technique applicable to ion groups. Thus, in the model given in the present application, tuning for calcium ions simultaneously enables one to tune for iron, nickel, cobalt, lithium and hydrogen ions, which are also at resonance under those conditions.

Once the effect has been shown for parallel fields, one can use the orientation of the fields for controlling the effect.

In some cases exposures for optimal effect must not be done at exactly the predicted maximum effect conditions, but at a slight variation from the maximum on either side. The IPR model clearly describes the magnitude of the required changes rather than either not acknowledging this issue or requiring substantial searching at nonspecific steps in magnitude. That is, when no effect is seen at $2B_{ac}$ $(pk)/B_{dc}=1.8$, then one can vary the effect slightly.

Another way of expressing this is that as $B_{ac}$ increases (with $B_{dc}$ and $f_{ac}$ held constant), the effect on the unhydrated ion in the system also increases in a predictable, nonlinear manner until $2B_{ac}$ $(pk)/B_{dc}$ is approximately 1.8. Then as $B_{ac}$ increases (again, with $B_{dc}$ and $f_{ac}$ held constant), the effect on the biological or chemical system generally decreases until $2B_{ac}$ $(pk)/B_{dc}$ is 3.8, at which point there is no change from the unexposed situation. The IPR model continues to predict effects for exposures beyond this value. Because the IPR model is explicit in its predictions, if a compensating mechanism is observed over some range of $B_{ac}$, one may still test for applicability of the IPR model at other values of $B_{ac}$ with minimal experimentation.

BRIEF DESCRIPTION OF THE DRAWINGS

FIG. 4 shows the results of Test 4.

FIG. 5 shows the ad hoc fit of an IPR model to acquired data.

DETAILED DESCRIPTION OF THE INVENTION

Figure 1:
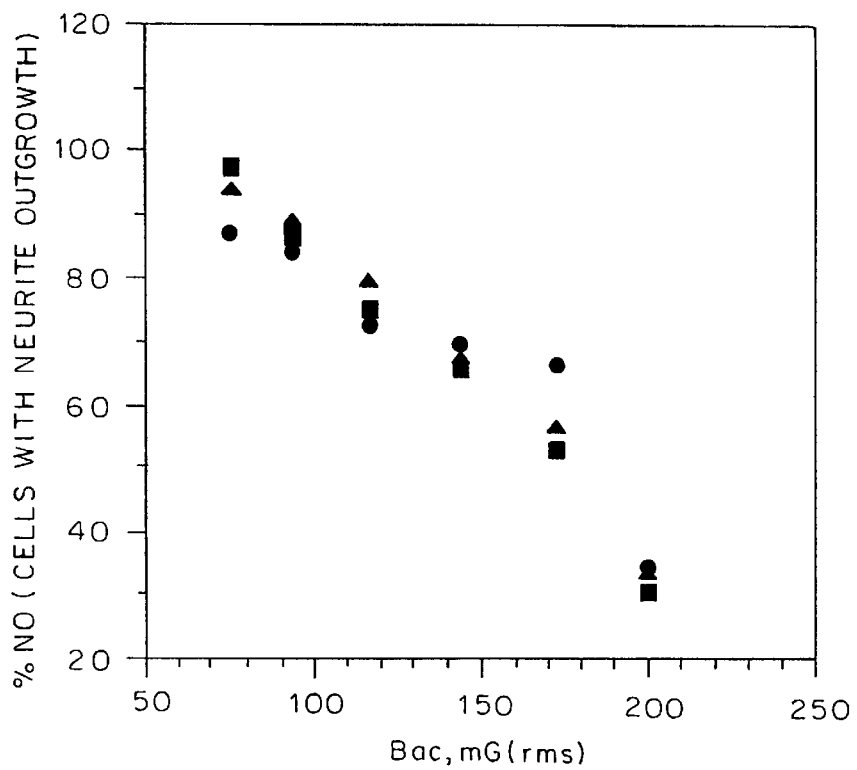
FIG. 1 shows the results of Test 1 for inhibition of percent neurite outgrowth stimulated by nerve growth factor in PC-12 cells exposed to 45 Hz sinusoidal magnetic fields between 77 and 200 mG(rms) [108–283 mG(pk)].

Ions have roles in both chemical and biological processes, from driving and catalyzing chemical reactions in chemical systems to controlling reactions within biological systems. It is well established that biological activity is driven by enzymatically controlled chemical reactions, and that some enzymes incorporated specific ions as cofactors to initiate or modulate their reaction rates. The role of other specific ions can be seen in selective functions of proteins, such as those involved in electron or oxygen transport.

Ionic cofactors and reaction centers and their dynamic interactions driven by thermal motion are critical elements in biological activities. At biologically relevant temperatures the enzyme molecules are immersed in a bath of solute molecules vibrating at infrared frequencies. Thus, it follows that ionic cofactors, their associated enzymatic reaction centers, and their dynamic interactions driven by the ever present thermal bath, are critical elements in biological activities. Native proteins at biologically relevant temperatures are not static forms, but fluctuate constantly, passing though a variety of similar configurations due to thermal influence. Karplus and Petsko (1990) point out the importance of this kinetic view of proteins by stating that "it would not be surprising if internal motions had been subjected to selective pressure during evolution. Just as structure is selected on the basis of function, there could be selection for certain internal motions, a consequence of the structure, if they had specific functional roles." Thus, thermally driven kinetic motion is an essential element of protein function, with functional selection of specific motions of forms evolving over time.

Many selective forms can be influenced by magnetic fields according to the present invention. For example, some enzymes have ligand-bound ions that can impart stability and conformational changes necessary for reaction sites to orient to optimal enzymatic activity. Frauenfleder et al. (1988) note that different conformational states of a working protein have the same overall structure and function but have varying structural details and rates at which the function is performed. Bialek et al. (1989) suggest that the most important enzyme configurations are those that reflect the optimal compromise between structures with high reaction probability and small strain energy in the protein. Specific details of the protein dynamics, particularly as they apply to functional properties of systems, remain unclear, although details of ion-enzyme interactions are being studied using synthetic peptides to provide a more explicit description of the interaction of ions and the binding sites in proteins (Regan, 1993).

However, the dynamic view of conformational states is important (Karplus et al., 1987). The interaction of an ion with its ligands in a protein can be viewed as an oscillator with a characteristic set of vibration frequencies (or, alternatively, a characteristic set of energies). Changes in protein function or enzyme activity are presumably a function of various minor structural or conformational states assumed by the protein represented by changes in energy levels of the reaction sites. Ions can have substantive roles as cofactors in establishing the appropriate conformational state or dynamic structure. Thus, thermal energy in active biological systems is normally present to promote random transitions between protein energy levels.

Changes in ion energetics caused by imposition of magnetic fields involves protein dynamics and leads to changes in enzyme kinetics. Thermal motions of solute molecules are relatively broad-band, nonspecific influences on enzyme-ionic cofactor complexes. It is possible that a critical ion may be bound in a protein cavity that shields it from collisions with solute molecules and precludes hydration of that ion. Consistent with the comments by Karplus and Petsko (1990), the present inventors have speculated that the natural vibration modes of the protein, particularly the ion cavity and the active site, may have evolved in tune with the vibrational modes of the specific ionic cofactor. It may be that these preferred vibratory modes for enzymatic activity are a consequence of ion cofactor binding. These modes can then be altered when the protein is bound to an ion at a predetermined site. Assuming that vibrational modes in enzymes contribute to their activity, then ion cofactor binding can be used to switch the activity on or off. Thus, the action of thermal energy from solution molecules surrounding the protein may not only promote random transitions between protein energy levels, but also supply energy to specific vibratory modes in the ion-enzyme complex that are critical for enzyme activity. From this perspective, resonant interactions of magnetic fields with a critical bound ion could conceivably alter the vibrational dynamics between this ion and its protein ligand(s) by splitting and modulating the energy states of this complex. Thus, fields might sufficiently alter the spatial and temporal aspects of the vibratory interaction process, the resident times at given levels, the number of levels, or the relative occupation of different levels sufficiently to distinguish the effect from random variations in these quantities. These changes could be accomplished by exceedingly small, frequency-specific amounts of energy over substantial periods of time. A change in the dynamic structure of the ionic complex could then lead to a change in the dynamic structure or the vibratory mode of the enzyme reaction site, which could lead to altered biochemical activity. This view of the dynamic interaction between proteins and ions appears to provide a critical element of magnetic field perturbations of the systems such as those described by the Edmonds (1993) and IPR models.

IPR Model Development

The IPR mathematical model used herein, Blanchard and Blackman (1984) and Blanchard et al. (1994 a, b, c), predicts very distinct responses that are consequences of multiple, independent variables of exposure including the DC, or static, magnetic field flux density as well as the AC magnetic field flux density, frequency, and relative orientation to the DC magnetic field. To control the response, one merely need obtain no more than three measurements to obtain a curve to determine if the system responds to the magnetic fields imposed thereupon. Once one knows that the system responds, using the IPR, one can control the response of the system.

There is support from a variety of sources for considering the influence of each of these parameters on biological systems, but the IPR mathematical model is the first to assemble them in a coherent, experimentally accessible manner and to provide a clear indication of the expected magnitude of result, relative to that of an unexposed sample, for any given combination of the independent variables. The IPR model, in its simplest form, for example, assumes an effect on an enzyme that is complexed with an ionic cofactor to preform its catalytic function in some reaction pathway. Magnetic fields, under conditions described by the IPR model, cause minor but significant changes in the ionic interaction with the enzyme that can alter its rate of reaction. This altered reaction rate can have biological consequences for the whole cell, and consequently for the organism.

The IPR mathematical model is based upon an earlier derivation of the influence of parallel exogenous AC and DC magnetic fields at the atomic level by Podgoretskii and Khrustalev (1964). Podgoretskii's derivation for atomic spectroscopy was extended to biological systems by Lednev (1991). Lednev's model contained some critical mathematical errors and focussed strictly on a limited set of ions that could be bound to the $Ca^{++}$binding protein. The present inventors have corrected the errors in the Lednev model, extended the set of ions potentially influenced by magnetic fields, and described the expected response form when the energy levels of two or more resonant ions are altered by external magnetic fields.

As originally formulated by Podgoretskii, an external DC magnetic field creates a Zeeman splitting of the quantum energy levels of each ion. These split energy levels are then frequency modulated by an external AC magnetic field. The involvement of frequency modulation suggests that the IPR response is distinct from the random effects of amplitude modulated thermal noise. Frequency modulation does not require addition of kinetic energy to the system. Rather, frequency modulation locally alters the potential energy of the system. The IPR mathematical model indicates that, although the potential energy alteration may be small on the global scale (and certainly less than the overall thermal noise level), the resultant small changes created locally in the population distributions may be significant in producing specific biological effects if associated with an ion resonance.

A fundamental parameter of the IPR mathematical model is the frequency index, which is the ratio of the ion's characteristic resonant frequency, $f_c$, to the frequency of the AC magnetic field oriented parallel to the DC magnetic field, $f_{ac}$:

$$n=f_c/f_{ac} \qquad (1)$$

where the frequency $f_c$ is coincidentally the same as the cyclotron resonance frequency, involving the ratio of an ion's charge (q) to its mass (m), or $$f_c=qB_{dc}/2\pi m \qquad (2)$$

Here we rename $f_c$ the characteristic resonant frequency in order to avoid confusion with Liboff's ion cyclotron resonance models. Within the IPR model, the critical term is n, describing the key relationship between system specific (ion) parameters (q/m) and externally imposed conditions ($f_{ac}$ and $B_{dc}$). Note that IPR model harmonics (n=1, 2, 3, . . .) are inverse to harmonics described by the ICR model (discussed below); this fact is critical to the predictions of the IPR model. In the IPR mathematical model, n defines an ion resonance condition associated with a specific splitting of an energy level, arising from the applied DC magnetic field.

The IPR mathematical model examines how the probability of ion transitions to lower energy levels changes when the ion is near resonance. According to the IPR model, the probability of ion transition, p, is given by the equation $$p=K_1+K_2\times(-1)^n\times J_n(n\times 2\times B_{ac}/B_{dc}) \qquad (3)$$

only when the ion's frequency index is integer valued ($J_n$ is the Bessel function of the first kind, order n; $B_{ac}$ is the peak AC flux density; and $B_{dc}$ is the DC flux density). $K_1$ is the response of the system when $B_{ac}=0$ and $K_2$ is a real constant whose value calibrates the contribution of the particular ion[s] to the biological or chemical endpoint as measured. The IPR mathematical model predicts that for ions with non-integer frequency indices, p will equal $K_1$ (a constant that is independent of $B_{ac}$).

Essentially, the IPR mathematical model predicts that when the applied DC field and AC frequency create a resonant environment for an unhydrated ion, or an entity with the same charge to mass ratio as an unhydrated ion, the probability of transitions between energy states associated with that ion or entity will be modified in a deterministic way. The modification for that ion is proportional to a Bessel function whose order is selected by the ion's integer-valued frequency index, n. Whether the contribution from the Bessel function is additive or subtractive, at least at the atomic level, is also determined by the integer value of n, with odd integer values inverting the sign of the Bessel function because of the $(-1)^n$ term. This distinction is expected to be significant primarily at the molecular level since at more complex levels (cellular, organ, or organism), molecular actions may reinforce or restrain the selected biological/chemical endpoint.

There is a distinction in the treatment of harmonics between the ICR and the IPR mathematical models. The ICR model postulates resonance-type effects when the AC frequency is some integer multiple of the fundamental ICR frequency ($f_{ac}=k \times f_c$ where k= any integer, and $f_c$= fundamental ICR frequency). By contrast, the IPR model derives a relationship between the fundamental ICR frequency, $f_c$, and integer multiples of the applied AC frequency that is the inverse of ICR model harmonics. A special case occurs at n=1, where the IPR predicted resonance is also an ICR mathematical model resonance. This means that for a given Bdc, the IPR model predicts effects at lower frequencies than would be recognized by the ICR model. Conversely, for a given fac, the IPR model predicts effects at higher Bdc values than are recognized by the ICR model. At harmonics of the ICR model, particularly for hydrogen ions, the IPR model predicts an off-resonance type of effect which is very different from ICR model predictions.

The IPR model is further distinguished from the work of Liboff et al. by its continuous predictions (mathematical function) of distinct response differences from the non-exposed state as $B_{ac}$ is increased. Aside from an ambiguous postulation of effect at $B_{ac}=B_{dc}$ (where $B_{ac}$ is interpreted as peak or rms value by different authors), the ICR model is mute on this issue.

Equation 3 differs from the original Lednev formulation in two critical ways: there is an additional $(-1)^n$ term on the right side of the equation; and the argument to the Bessel function contains an additional factor of 2.

Although the Lednev model focused on magnetic field effects on calcium binding proteins, the IPR model does not require or exclude calcium except by its resonance characteristics. The IPR model explicitly recognizes that a system's response may reflect the combined influence of several different near resonance ions. In the absence of contrary information, ions are assumed to act independently to produce the observed response, and the IPR model predicts that the response will be a linear sum of the individual response functions uniquely characteristic of the ions within the system. As explained in more detail later, hydrogen is an exception.

In applying the IPR mathematical model to complex biological systems, the ions at resonance are assumed to be in the unhydrated state. This situation may be found, for example, when transition metal ions are loosely bound by ligands in a molecular structure. Table 1 lists biologically significant ions (compiled from Liboff, 1985, 1992; Liboff and Parkinson, 1991; EPRI, 1990; Abrams and Murrer, 1993; Karlin, 1993; Lippard, 1993; O'Halloran, 1993; Pyle, 1993; Regan, 1993; Thomas et al., 1986) for which IPR model predictions have been made, and shows how the frequency index for each ion changes with variations in either the flux density of the DC magnetic field or the AC magnetic field frequency. This table is not an all inclusive list. Appearance of an ion in Table 1 indicates a potential biological role but does not imply significant activity of any particular ion in a given system. To maximize the number of possible options, the present inventors have included all valences and have not limited the selection to the oxidation states normally considered biologically relevant, as these may exist momentarily in some biological/chemical systems as intermediate states and could be affected by the imposition of a magnetic field. Moreover, on a strictly chemical, i.e., non-biological system, there is no need to consider biological relevance. In addition, the masses used are for unhydrated ions, as required by the model and supported by the work of Chiabrera and Bianco (1991); otherwise, the effective ionic mass could be infinitely variable.

TABLE 1

Frequency Indices for Various Potential Biologically Significant Ions

| Ion Name & Valence | q/m C/kg*$10^6$ | $f_{ac}$ = 45 Hz $B_{dc}$ = 370 mG | $f_{ac}$ = 25 Hz $B_{dc}$ = 205.5 mG | $f_{ac}$ = 45 Hz $B_{dc}$ = 575 mG | $f_{ac}$ = 45 Hz $B_{dc}$ = 20 mG |
|---|---|---|---|---|---|
| Lead 2 | 0.925 | 0.121 | 0.121 | 0.188 | 0.007 |
| Barium 2 | 1.395 | 0.183 | 0.183 | 0.284 | 0.010 |
| Copper 1 | 1.510 | 0.198 | 0.198 | 0.307 | 0.011 |
| Cadmium 2 | 1.700 | 0.222 | 0.222 | 0.346 | 0.012 |
| Lead 4 | 1.850 | 0.242 | 0.242 | 0.376 | 0.013 |
| Strontium 2 | 2.187 | 0.286 | 0.286 | 0.445 | 0.015 |
| Potassium 1 | 2.450 | 0.321 | 0.321 | 0.498 | 0.017 |
| Chlorine 1 | 2.720 | 0.356 | 0.356 | 0.553 | 0.019 |
| Zinc 2 | 2.940 | 0.385 | 0.385 | 0.598 | 0.021 |
| Copper 2 | 3.020 | 0.395 | 0.395 | 0.614 | 0.021 |
| Cobalt 2 | 3.250 | 0.425 | 0.425 | 0.661 | 0.023 |
| Nickel 2 | 3.260 | 0.427 | 0.426 | 0.663 | 0.023 |
| Iron 2 | 3.430 | 0.449 | 0.449 | 0.698 | 0.024 |
| Manganese 2 | 3.490 | 0.457 | 0.457 | 0.710 | 0.025 |
| Chromium 2 | 3.680 | 0.482 | 0.481 | 0.748 | 0.026 |

TABLE 1-continued

Frequency Indices for Various Potential Biologically Significant Ions

| Ion Name & Valence | q/m C/kg*$10^6$ | $f_{ac}$ = 45 Hz $B_{dc}$ = 370 mG | $f_{ac}$ = 25 Hz $B_{dc}$ = 205.5 mG | $f_{ac}$ = 45 Hz $B_{dc}$ = 575 mG | $f_{ac}$ = 45 Hz $B_{dc}$ = 20 mG |
|---|---|---|---|---|---|
| *Vanadium* 2    | 3.762  | 0.492  | 0.492  | 0.765  | 0.027 |
| *Arsenic* 3     | 3.836  | 0.502  | 0.502  | 0.780  | 0.027 |
| *Sodium* 1      | 4.180  | 0.547  | 0.547  | 0.850  | 0.030 |
| *Calcium* (45) 2| 4.290  | 0.561  | 0.561  | 0.872  | 0.030 |
| *Calcium* (40) 2| 4.780  | 0.626  | 0.625  | 0.972  | 0.034 |
| *Cobalt* 3      | 4.880  | 0.639  | 0.638  | 0.992  | 0.034 |
| *Nickel* 3      | 4.900  | 0.641  | 0.641  | 0.996  | 0.035 |
| *Iron* 3        | 5.150  | 0.674  | 0.674  | 1.047  | 0.036 |
| *Manganese* 3   | 5.230  | 0.684  | 0.684  | 1.064  | 0.037 |
| *Chromium* 3    | 5.530  | 0.724  | 0.723  | 1.125  | 0.039 |
| *Vanadium* 3    | 5.642  | 0.738  | 0.738  | 1.147  | 0.040 |
| *Molybdenum* 6  | 5.992  | 0.784  | 0.784  | 1.219  | 0.042 |
| *Arsenic* 5     | 6.394  | 0.837  | 0.836  | 1.300  | 0.045 |
| *Manganese* 3   | 6.980  | 0.913  | 0.913  | 1.419  | 0.049 |
| *Vanadium* 4    | 7.523  | 0.984  | 0.984  | 1.530  | 0.053 |
| *Magnesium* 2   | 7.890  | 1.032  | 1.032  | 1.605  | 0.056 |
| *Vanadium* 5    | 9.404  | 1.231  | 1.230  | 1.912  | 0.067 |
| *Manganese* 6   | 10.500 | 1.374  | 1.374  | 2.135  | 0.074 |
| *Chromium* 6    | 11.100 | 1.453  | 1.452  | 2.257  | 0.079 |
| *Sulphur* 4     | 11.954 | 1.564  | 1.564  | 2.431  | 0.085 |
| *Manganese* 7   | 12.200 | 1.597  | 1.596  | 2.481  | 0.086 |
| *Lithium* 1     | 13.800 | 1.806  | 1.805  | 2.805  | 0.098 |
| *Sulphur* 63    | 17.930 | 2.346  | 2.346  | 3.646  | 0.127 |
| *Hydrogen* 1    | 95.600 | 12.510 | 12.507 | 19.442 | 0.676 |

For example, allowing a ±10% resonance bandwidth, the near-integer-valued frequency indices, n, when $B_{ac}$=370 mG and $f_{ac}$=45 Hz are 1 (Mn4, V4, and Mg2) 2, (Li) and 12 (hydrogen). For $B_{dc}$=575 mG and $f_{ac}$=45 Hz, the possible frequency indices are 1 (Ca2, Co3, Ni3, Fe3, Mn3), 3(Li), and 19 (hydrogen). According to the IPR mathematical model, variations in $B_{dc}$ or in $f_{ac}$ individually will change the ions for which frequency indices are near integer value, while proportional changes in $B_{dc}$ and $f_{ac}$ will maintain the selection. For example, the ratio of 370 to 45 is the same as the ratio of 205.5 to 25, so the frequency indices and resonant ions for those two combinations are identical. Since the mathematical model is selective for ions solely on the basis of their charge to mass ratio, effects on ions with exactly the same frequency index will be indistinguishable except if the measured endpoint is known to be influenced by a particular ion. Ions with closely related frequency indices at given values of $B_{dc}$ and $f_{ac}$ can most easily be distinguished at higher $B_{ac}$ flux densities.

Effects predicted by the IPR mathematical model are most easily tested when exposure values create resonance conditions for either a single biologically significant ion or only one near-integer-valued frequency index. When the exposure values create resonance conditions for a variety of ions representing several frequency indices, the resulting response function may become quite complex, requiring a number of exposure test points on the order of the number of distinct frequency indices to sample that response function unambiguously.

The enhanced sensitivity predicted by the IPR mathematical model for small changes in $B_{ac}$ as $B_{dc}$ approaches zero is limited by the finite bandwidth of ionic resonances.

Control of the AC frequency and the DC field strength so as to create a resonance for an ion suspected to be active in the creation of said biological/chemical action within the biological/chemical system is such that the ratio of the ion's charge to its mass is an integer multiple of the ratio of the angular frequency of the AC magnetic field ($2* \pi * f_{ac}$) to the flux density of the DC magnetic field. The resonance claimed here is the mathematical inverse of the Ion Cyclotron Resonance already addressed by Liboff et al. Therefore, they are the same ONLY when the integer value of the present claim is uniquely one. Further, the ions considered by ICR are a subset of those specified by IPR. An ion may be suspected to be active as a result of previous research (see for example the list of ions identified through other studies as having potential biological significance given as Table 1 of this application), or it may be identified as a result of testing for other ions (see for example the work of Blackman et al. (1994) that identified hydrogen as a potentially significant ion and the subsequent work by Trillo et al. (1994) confirming a biological role in accordance with the claims of this application).

IPR Mathematical Model Application

Although there are three apparently independent variables in the IPR mathematical model, they are coupled within the model, so tests to demonstrate clear consistency with IPR model prediction must consider the interrelated nature of the variables. The basic tests are described below, beginning with variations in $B_{ac}$, to determine whether the response observed in a particular biological system is consistent with the predictions of this IPR model.

In any test or use of the IPR model, it is critical that the magnetic fields to which the biological systems are exposed are only those required by the model. Thus, it is essential that the nonparallel component of the DC magnetic field be reduced to as close to zero as possible.

Changes in $B_{ac}$ $B_{ac}$ is the only variable unrelated to ion selection, because it appears only in the argument of the Bessel functions. Thus, a test that examines a range of $B_{ac}$ exposures while maintaining $B_{dc}$ and $f_{ac}$ constant provides a quick test of IPR applicability. The $f_{ac}$ and $B_{dc}$ values should be selected so that at least one ion that is expected to be active in the system under test has a near-integer-valued frequency index. Multiple test points are generated by varying $B_{ac}$ such that the tests examine exposures for which $n \times 2B_{ac}/B_{dc}$ varies from near zero, i.e., $B_{ac}$= zero, to at least the first zero crossing of the least-order-selected Bessel function (i.e., the least-valued near-integer frequency index, determined by the selected values of $B_{dc}$ and $f_{ac}$). For example, if the least valued near integer frequency index is 1 (n=1) then the least-order Bessel function selected is $J_1$, and the argument range over which one would observe an effect increasing to a maximum and then returning to no effect would be $n \times 2B_{ac}/B_{dc}$=0–3.8. For example, one can establish $K_2$ at values of $2nB_{ac}/B_{dc}$=1.4, 1.8, and 2.3, which then calibrates all subsequent predicted responses. The predicted system response over this range, assuming either a minimum of other near-integer frequency indices, or dominance of the $J_1$ based response, is approximately U-shaped (see FIG. 5a). It should be noted that the value of $K_1$ (determined by the sham response for no AC field exposure) sets the starting point and the value for $K_2$ varies the depth of variation for the response associated with ion(s) having a common near-integer-valued frequency index (equation 3), but neither coefficient changes the relative positions of the minima, maxima, or "zero crossings" (null effect relative to unexposed system) of the predicted IPR mathematical model response function. In fact, since the value of $K_1$ is established directly by control data, there is only one variable ($K_2$) per frequency index that can be adjusted to fit the acquired data. When $B_{dc}$ and $f_{ac}$ are selected such that no ion is at resonance, changes in $B_{ac}$ are not predicted to alter the observed response, as discussed above and in the next section.

Changes in $B_{dc}$

Varying $B_{dc}$ by itself would bring different ions on and off resonance, changing their frequency indices in the process. Since the IPR mathematical model predicts a flat response (p= constant) when no ion is at resonance, detuning for all ions through an appropriate selection of the DC flux density tests the IPR model while eliminating one of the variables in which $B_{dc}$ plays a role (no Bessel function is selected, so there is no influence on the argument). This provides a second critical test of IPR model applicability. Hydrogen provides the limiting case: its charge to mass ratio is the largest possible of all elements and it is a potential biologically significant ion. For the "off-resonance" test, $B_{dc}$ is chosen and fixed such that the frequency index for hydrogen is well below unity, and the same $f_{ac}$ used in the previous test is maintained in this test. Given these fixed parameters, test points should be generated to test the system response over a range of Bessel function arguments ($n \times 2 \times B_{ac}/B_{dc}$) comparable to those tested in the previous case. The predicted system response under these conditions is flat, with no variation across the entire range of AC field values tested (see FIG. 5b).

Changes in $f_{ac}$

Finally, the effects observed in the preceding tests must be consistent across a variety of AC frequencies. Variations strictly in the AC field frequency, $f_{ac}$, would change two components of the IPR model: the near-integer frequency indices and the argument to the selected Bessel functions. If only $f_{ac}$ were varied during such tests, the results would be complicated to interpret in terms of the IPR model, because it would change the frequency index for each ion, could select a different Bessel function, and would form a different Bessel function argument. A cleaner test examines the consistency of response when both the AC frequency and the DC flux density change proportionally to maintain the frequency indices selected in the first test. This is critical, in that the effects observed in the earlier tests are specifically a function of the active ions selected. Test points should then be generated to give the same argument to the Bessel function(s) as in the first test. In essence, this performs the first test at a different frequency. The predicted response function is the same as that predicted for the first test (e.g., U-shaped if the $J_1$ term is dominant).

Using the three critical tests described above, one skilled in the art can readily identify whether a biological system's response to parallel AC and DC magnetic fields is consistent with the IPR mathematical model. These tests are based upon controlled variations in three basic parameters: the flux densities of parallel components of the AC and DC magnetic fields and the AC magnetic field frequency to examine on and off resonance cases. For "on resonance" tests, the response forms are distinctly nonlinear. The "off resonance" response is predicted to be flat across a range of AC flux densities, in stark contrast to the "on resonance" case. Once a system is shown to respond consistently with IPR model predictions, as described above, clear and distinct predictions can be made about its expected response to different values of $B_{ac}$, $f_{ac}$ or $B_{dc}$.

The following description is one of many possible embodiments of the present invention by which controlled magnetic field exposures can be created. This description is included merely for illustration, and not for limitation.

A pair of Helmholtz coils, consisting of two 100-turn, 20-cm diameter coils of enameled wire (22 awg; 35 ohms resistance per coil), aligned coaxially 10 cm apart, were oriented and energized to control the vertical DC and AC magnetic fields (cf. Blackman et al., 1994). As needed, both coils were energized with a direct current to adjust the ambient, vertical DC magnetic field in the sample area. Only the lower coil was energized with AC current to create sinusoidal magnetic fields of decreasing strength on the coil axis as a function of distance above the coil. The six PC-12 samples to be exposed were placed coaxially with the coil center line. In some cases a seventh dish was added within the stack to provide the desired range or spacing of $B_{ac}$. To reduce the horizontal components of the ambient DC magnetic fields to values as low as possible (<2 mG), two square coils, 27 cm on a side and separated by 17 cm wound with 200 turns of enameled wire, were included as part of the exposure system.

The exposure system, consisting of the coil systems and cell samples, was located on a plastic shelf in the upper two-thirds of the incubator space. A Co-magnetic metal magnetic-field shield (Magnetic Shield Corp.) created a shielded area, also within the incubator, to serve as a control, or unexposed, area. This shield reduced the flux density of the magnetic field generated by the exposure system to less than 1% (cf. Blackman et al., 1994). The Co-netic shield was in a tube configuration position near the bottom of the incubator space, with the long axis fore and aft to allow for air circulation and ease of positioning the dishes. No temperature differences greater than 0.1° C. (resolution of meter) were observed using Chromel-Alumel thermocouples between different samples in the coils, with the coils energized at the highest currents used. No temperature differences were observed between the exposed samples and the shielded samples. Sham exposures revealed no difference in cell response between exposure and shielded positions.

A function generator and an ampmeter, connected in series with the lower circular coil, produced and monitored the sine wave current and, as needed, the desired direct current. Measurements with a frequency meter verified the proper setting on the function generator. All generating and monitoring equipment was located outside the incubator.

The AC magnetic fields cited in these experiments were verified at the locations of each dish with a calibrated gaussmeter (Bell 640) and Hall effect probe. When the coils were placed in the $CO_2$ incubator, the proximity of the inner walls reduced the actual flux density at the test specimen locations by approximately 20% from the calculated values. The measurements reflect this reduction, and are cited as root-mean-square (rms) values read from the gaussmeter, with their corresponding peak (pk) equivalents given in parentheses.

Empirical Test of IPR Model Interactions

The response of PC-12 cells under the exposure conditions suggested is described below and finds clear consistency with the IPR model. The following descriptions are only some of many possible embodiments of the present invention by which the IPR model can be shown to predict or to measure a biological response to controlled parallel AC and DC magnetic fields. These descriptions are included merely for illustration, and not for limitation. The predictive nature of the model is discussed after detailed demonstrations of the IPR model consistency.

The PC-12 cell line was used for the following experiments. The neurite outgrowth (NO) the cells display in response to stimulation by nerve growth factor (NGF) has served as a basis world-wide for investigations of NGF-induced changes in nervous system-derived cells (Levi et al., 1988) since Greene and Tischler (1976) first established the line from a rat adrenal pheochromocytoma. The PC-12 assay system has been shown previously to be differentially responsive to AC magnetic fields. The assay is simple, well established, and widely used among those skilled in the art of neuroscience. Because this system examines functions at the isolated, single-cell level, its simplicity is of considerable advantage to theoreticians studying the interactions of electromagnetic fields with biological systems. This neurite outgrowth assay system is currently used to evaluate neurotransmitted production and second messenger signalling processes and subsequent genomic events, particularly those induced by nerve growth factor stimulation.

Earlier tests demonstrated that NGF-stimulated neurite outgrowth in PC-12 cells could be inhibited by exposure to 50 Hz magnetic fields during a 22-hour treatment period (Blackman et al., 1993). The response demonstrated a magnetic field strength dependence across the range of 35–90 mg(rms) [3.5 and 9.0 $\mu T$(rms)]. The inhibition was further shown to be independent of any induced electric field. In addition, there was an observed dose rate dependence of this inhibition over the frequency range of 15–70 Hz. These exposures consisted of a vertical AC magnetic field with an ambient static DC magnetic field, wherein the DC field contained both vertical and horizontal components. At the time, there was no apparent explanation for the observed changes in neurite outgrowth in C-12 test cells.

Materials and Methods

Growth and Preparation of Cells

The PC-12 cells used in these experiments were obtained from the Tissue Culture Facility at the University of North Carolina at Chapel Hill. The cells were primed by growth in RPMI 1640 medium (Gibco 320–1875), supplemented with 10% horse serum (Gibco 200–650), and 5% fetal calf serum (Gibco 240–6000), and 100 units/ml each of penicillin and streptomycin on six-well collagen coated plates (Costar 3046) in a 5% $CO_2$ incubator at 37° C., with addition of NGF (50 ng/ml, 2.5 S, Sigma 6009) at plating and every other day for six days. On day 7, the medium was removed from the primed cells, and the cells were washed three times with complete medium to remove any remaining NGF. The cells were then removed from the plates by trituration, centrifuged, resuspended, counted, placed into 10% dimethylsulfoxide (DMSO), frozen, and stored at −80° C. in 1 ml volumes of $1 \times 10^6$ cells/ml. Prior to each experiment, the cells were thawed and rinsed with medium three times, and the contents of one ampoule were placed into 50 ml of medium.

The collagen-coated petri dishes were prepared by placing 0.45 ml of stock solution [5 mg of collagen (Sigma rat tail type VII 8897) in 125 ml of 0.1M acetic acid] on 60 mm dishes (Costar 3060). The dishes were then air dried in a sterile hood. Before use, the dishes were rinsed with medium to neutralize the pH. Five milliliter volumes of primed cells, at $2 \times 10^4$ cells/ml, were plated onto 60 mm collagen-coated petri dishes. At this plating density, the cells covered less than 10% of the growth surface.

The cell medium was supplemented with 5 ng/ml of NGF (Sigma 6009) for all but the zero NGF control. This NGF concentration had previously been shown to induce neurite outgrowth in approximately 50% of the cells (Blackman et al., 1993). All dishes in the exposure system contained 5 ng/ml of NGF. To establish the control parameters in each experiment, two dishes with and two dishes without NGF were placed within the control (nonexposed) area in the same incubator. The one exception to this occurred for one trial each of tests 1 and 2, when only one dish was used for each control condition.

Magnetic Field Exposure System

The PC-12 cells were exposed to prescribed sets of parallel AC and DC magnetic fields while housed in a 5% $CO_2$ incubator maintained at 37° C. Prior to testing, the ambient AC and DC fields were measured with a Bartington MAG-03 fluxgate magnetometer. The ambient DC magnetic field within the exposure apparatus was 447 mG at an inclination of 60°N. (389 mG vertical and 220 mG horizontal). The ambient 60 Hz magnetic field in the exposure apparatus was 8.8 mG(rms) [7.0 mG(rms) vertical and 5.3 mG(rms) horizontal], whereas within the shielded area it was 1.2 mG(rms) [0.74 mG(rms) vertical and 0.92 mG(rms) horizontal].

Exposure

The PC-12 cells were exposed for 23 hours, beginning within three minutes after plating, to examine responses to four distinct tests, shown in Table 2. (Note that these conditions did not tune for calcium ions.) The observed effects were both consistent with the predictions of the IPR mathematical model and confirmed the validity of extending the ion list beyond calcium. Additionally, the repeatability of the results was checked by running tests 1, 3 and 4 three separate times and tuning test 2 four times. For every exposure, two sets of controls were placed in the shielded area: one set with and one set without NGF.

TABLE 2

Exposure Conditions

| Critical Quantity | Units | Test 1 | Test 2 | Test 3 | Test 4 |
|---|---|---|---|---|---|
| AC frequency | Hz | 45 | 45 | 45 | 25 |
| $B_{dc}$-horizontal ($B_{dc}H$) | mG | <2.0 | <2.0 | <2.0 | <2.0 |
| $B_{dc}$-vertical ($B_{dc}V$) | mG | 366 | 366 | 20 | 203 |
| $B_{ac}$-vertical (min) | mG rms (pk) | 77 (108) | 200 (284) | 7.9 (11) | 78 (110) |
| $B_{ac}$-vertical (max) | mG rms (pk) | 200 (283) | 468 (662) | 21 (29) | 181 (256) |
| $B_{ac}V(rms)/B_{dc}V$ range | — | 0.21–0.55 | 0.55–1.28 | 0.40–1.03 | 0.30–0.89 |
| $B_{ac}V(pk)/B_{dc}V$ range | — | 0.30–0.78 | 0.78–1.81 | 0.54–1.41 | 0.54–1.26 |

A common reference point was selected, consisting of an AC frequency of 45 Hz for tests 1–3, $B_{dc}$ V of 366 mG (ambient) for tests 1 and 2, and a horizontal DC flux density ($B_{dc}H$) reduced to as close to 0 mG as possible (less than 2 mG in all experiments). All ions from Table 1 that were close to resonance for $B_{dc}$=366 mG and $B_{ac}$ at 45 Hz, and two ions that are far from resonance for these exposure conditions, are shown in Table 3, where n is the frequency index defined earlier. For test 4, the ratio of $B_{dc}$ to $f_{ac}$ is the same as for tests 1 and 2, so that Table 3 remains applicable. Test 3 was designed specifically for off-resonance conditions for all ions listed in Table 1.

TABLE 3

Ions Near and off Resonance

| Ion | Frequency Index, n |
|---|---|
| Ca (2) | 0.619 |
| Fe (3) | 0.667 |
| Mn (4) | 0.904 |
| V (4) | 0.974 |
| Mg (2) | 1.021 |
| Li (1) | 1.786 |
| H (1) | 12.375 |

In this example, Mn(4), V(4), Mg(2), Li(1), and H(1) are within 10% of an integer-valued frequency index. By contrast, Ca(2) and Fe(3) are well off-resonance. Note that, as either the DC field flux density or the AC field frequency changes, the number and closeness of ions to resonance conditions will vary. A more complete list of potentially biologically significant ions is given in Table 1 of this application.

Under the exposure conditions used in tests 1, 2 and 4, at least three ions from Table 1, manganese, vanadium, and magnesium, were within 10% of their predicted resonance peak for n =1. Although there is no a priori way of knowing that these ions are present or active in PC-12 cell generation of neurites, the fact that Landreth et al. (1990) and Sano (1992) identified magnesium and manganese as critical cofactors in the phosphorylation of microtubule-associated proteins in neurites that are induced by NGF stimulation suggests an enhanced possibility that an effect might be seen under the prescribed exposure conditions. In addition, at least three potentially significant ions that are near resonance, two of which are Mg and Mn, had the same frequency index. Two other potential biologically effective ions, calcium and iron, were far from resonance under these conditions. Lithium, with a frequency index near 2, is a candidate for effective ions whose frequencies can be altered by imposition of a magnetic field.

A variety of changes in experimental protocol designated here blind, double-blind, and triple-blind tested the IPR model were conducted using PC-12 cell responses to magnetic fields against the predictions of the IPR model under three levels of experimental blindedness. The blind test involved testing the response function, i.e., expected degree of cellular response, unknown to the person measuring the test results. The double-blind test was the same as the blind test plus the relative exposure levels were not know to those associated with the test. The triple-blind study was the same as the double-blind study plus an exposed and a sample blinded to those associated with the test.

For the test, PC-12 cells were exposed for 23 hours in a $CO_2$ incubator with or without controlled AC and DC magnetic fields. Quality control consisted of two controls (unexposed dishes of cells) with and without 5 ng/ml nerve growth factor (NGF) to determine how well the cell preparation responded to nerve growth factor. The raw percentage of cells/clusters meeting the neurite outgrowth criteria was evaluated. A positive score resulted if the neurite length was greater than one cell diameter. Over 200 cells/clusters in each dish were counted. A normalized result was expressed as a percentage of the range established by the controls.

The results of the blind experiments were consistent with the predictions of the IPR model across a wide range of parameter variations. Double-blind experiments demonstrated consistency with the results of the blind experiments, with minor exceptions. Triple-blind experiments unequivocally demonstrated a clear, distinctive, repeatable consistency with both the actual energization of the exposure systems and the predictions of the IPR model. In all four experiments, the energized system was correctly identified based on the predictions of the IPR model, and at least 19 of 20 exposed or sham-exposed dishes were correctly identified (p=0.000024).

The above demonstrated that the reported results are reliable and not influenced by the measurement technique. In fact, the results in the triple-blind experiments could have happened by chance a maximum of 24 times in 1,000,000 trials.

Melatonin Modulation of Reduction in Gap Junction Communication Due to Tumor Promoting Chemicals Melatonin is a naturally occurring hormone secreted by the pineal gland. Melatonin is known to have oncostatic properties at physiological concentrations. One action of tumor promoters (both known an suspected) in drinking water, such as perchloroethylene (PERC) and metabolites of dichloroacetic acid (DCA), trichloroacetic acid (TCA), chloral hydrate (CH), and trichloroethanol (TCEth) is interruption of gap junction intercellular communication.

Tests were conducted to examine whether melatonin at physiological concentrations can modulate the inhibition of intercellular communication cause by these chemicals in Clone 9 cell cultures (normal rat liver cells).

Intercellular communication was assayed by the scrape-load dye-transfer method using Lucifer Yellow. Concentrations of chemicals that had been shown to reduce intercellular communication in 24 hours by approximately one third compared to controls were selected. The chemicals and concentrations chosen were: DCA at 10 mM and 20 mM; TCA at 2.5 mM; CH at 5 mM; TCEth at 5 mM; and PERC at 0.1 mM. The doses or melatonin tested were in the physiological range: 1, 2.5, 5, 10, 20, 40 and $80 \times 10^{-10}$ M, with a maximum increase at $20 \times 10^{-10}$ M. Cells exposed to DCA at 20 mM demonstrated increased intercellular communication at melatonin concentrations of 10 and $20 \times 10^{-10}$ M. Intercellular communication in cells treated with TCA showed increased intercellular communication at melatonin concentrations of $2.5 \times 10^{-10}$ and at $10 \times 10^{-10}$ M with a maximum increase at $5 \times 10^{-10}$ M.

As reported in Carcinogenesis 16(12): 2945–2949 (1995), the entire contents of which are hereby incorporated by reference, melatonin was added to confluent fibroblasts at a concentration of $10^{-10}$ M. Twenty seven hours later, a fluorescent dye was scrape-loaded into groups of cells, and the transfer of the dye to adjacent cells through gap junctions was quantified. Under these conditions, melatonin induced a significant increase in dye transfer; this increase was not observed when the cultures were exposed to the magnetic field for 30 minutes before the scrape-load assay was performed. These data indicate that extremely low frequency magnetic fields could counteract the melatonin-induced enhancement of junctional transfer.

As demonstrated above, magnetic fields can remove the growth retarding activity of melatonin in MCF-7 cell growth. Since the growth retarding activity of tamoxifen, a chemotherapeutic agent, in MCF-7 human breast cancer cells has been shown to be removed by magnetic fields, one skilled in the art would thus expect the IPR model-defined exposure conditions to influence this action in precise ways depending on the specific exposure conditions. Specifically, it is possible to control the action of the magnetic fields to whatever level desired, and it is possible to localize the proper exposure conditions within an entity, e.g., a human, so as to treat only the desired volume within the larger biological sample.

Gap Junction Changes in Rat Liver Cells as Revealed by Magnetic Fields

It was found that gap junction communication could be reduced by suspected cancer promoting agents in general, and that magnetic fields were effective in modulating this reduction. Chloral hydrate was chosen as an example. In particular, the relative degree of influence of magnetic fields appeared to be very similar to that found for inhibition of nerve growth factor stimulated neurite outgrowth in PC-12 cells. Both were consistent with the predictions of the IPR model.

An epithelial rat liver cell line from the American Type Culture collection, designated Clone 9, demonstrated substantial functional intercellular communication when assayed by the Scrape/Load Dye Transfer technique developed by El-Fouley et al. (1987). Here, chloral hydrate was used to partially inhibit intercellular communication before the cells were exposed to 45 Hz $B_{ac}$ over a flux density range of 79–499 mG(rms) using a 366 mG parallel, <2 mG perpendicular $B_{dc}$. Following a 30-minute exposure, the dishes were examined for the transfer of the fluorescent dye, Lucifer Yellow. The exposure conditions selected were based on predictions of the IPR model to provide the familiar U-shaped response curve as a function of $2B_{ac}$ (pk)/$B_{dc}$. In the second set of experiments, exposures were selected to produce the maximum change in gap junction communication and used for various time periods to determine the time to maximum effect and, following exposure, for complete recovery in gap junction communication.

It was found that the transfer of dye away from the row of wounded cells at the scrape line was found to be consistently reduced in a dose-rate-dependent fashion precisely as predicted by the IPR model ($R^2=0.82$). When the parameters obtained for the best fit of the IPR model to the PC-12 cell results were used to analyze normalized gap junction communication data from the Clone 9 cells, the fit gave an $R^2$ of 0.74. When the model parameters were allowed to seek the best possible fit, the $R^2$ only increased to 0.78. Exposure under magnetic field conditions that produced maximum gap junction communication changes for times from 10 to 60 minutes showed no further change in gap junction communication after 30 minutes of exposure. After 30 minutes of exposure, recovery of gap junction communication was studied at five minute intervals to 45 minutes and again at 60 minutes. The cells had completely recovered 45 minutes after exposure was ended.

Two different assay systems, using different cells and different endpoints, responded to magnetic field exactly according to the non-linear predictions of the IPR model. Further, the parameters fixed by the best fit of the IPR model to the results of the PC-12 assay also fit the results of the Clone 9 assay very well without any parameter adjustments. This result extends the generality of the predictive nature of the IPR model. The Clone 9 cell assay is more rapid than the PC-12 cell used to hen this was used to quantify the kinetic nature of the field-induced effects. In both assay systems, the observed quantities are plasma-membrane based phenomena involving second messenger systems that may provide insight into the underlying molecular basis for this magnetic field effect. In both the Clone 9 cell assay and the PC-12 assays described above, the observed quantity was a plasma-membrane based phenomenon involving a second messenger system in the activation of the process.

In another experiment, Clone 9 cells (rat liver epithelial cell line) were treated with enough chloral hydrate for 24 hours to reduce gap junction communication by one third (5 ng/ml, Benane et al., 1996) and exposed to IPR model-described magnetic field conditions to produce the maximum effect on Mg/Mn ions AC frequency =45 Hz; $B_{dc}$=366 mG; $B_{ac}$=233 mG(rms). The cell samples were exposed for 10, 20, 30, 40 and 60 minutes, and the gap junction communication was measured. The cells responded maximally after 30 minutes of exposure.

Secondly, cells similarly treated with chloral hydrate were exposed for 24 hours to the same IPR model described magnetic field conditions for 30 minutes, and gap junction communication was assayed after various periods of time, from 5 minutes to one hour. The cells were seen to have partially restored gap junction communication within ten minutes after cessation of exposure, with no further restoration of gap junction communication until 40 minutes after cessation of exposure. These rapid changes in gap junction communication are accounted for by changes in phosphorylation of gap junction proteins, brought on by IPR-determined magnetic field induced changes in protein kinases of the signal transduction pathways, and subsequent phosphatase activity. Ion association with information processing components in the cells are the underlying bases for these results.

Orientation Significance in the Ion Parametric Resonance Model

Previous tests demonstrated the critical role of each of the following variables within the IPR model: $B_{ac}$, $B_{dc}$, $f_{ac}$ and q/m. Further testing was conducted to determine the importance of the relative orientation between $B_{ac}$ and $B_{dc}$.

An assay of neurite outgrowth from nerve growth factor stimulated, primed PC-12 cells was used to explore the effects of 23 hours of exposure to magnetic fields. Using a 45 Hz AC magnetic field over the flux density range of 132–344 mG(rms) (the range predicted by the IPR model to produce the maximal reduction in neurite outgrowth when in parallel with a DC field of 366 mG to give resonance conditions for Mg/Mn and H).

The following $B_{dc}$ values were tested:

(1) 366 mG parallel/<2 mG perpendicular to $B_{ac}$
(2) <2 mG parallel/366 mG perpendicular to $B_{ac}$
(3) 366 mG parallel/366 mG perpendicular to $B_{ac}$
(4) 366 mG parallel/160 mG perpendicular to $B_{ac}$ The experimental results showed that the expected U-shaped inhibitor response function with the DC field (366 mG) was parallel to the AC field, with the perpendicular DC field <2 mG. When the DC field orientation was reversed (parallel <2 mG, perpendicular 366 mG), the cell response showed an enhanced neurite outgrowth in the middle of the AC flux density range. Additional tests confirmed a statistically significant enhancement in neurite outgrowth at 202 mG(rms). Other tests conducted with different combinations of parallel and perpendicular DC flux densities showed that when the perpendicular DC field was present, it dominated the cell response function in an intensity-dependent manner.

From the above, it can be concluded that the differences seen in cell responses suggest a distinction in interaction models depending on the relative orientation of the AC and DC fields. Relative orientation of AC and DC fields is critically important and may provide a means of tuning the degree of response seen from a particular combination of fields (cf. Blackman et al., Bioelectromagnetics, 11: 159–167, 1990, the entire contents of which are hereby incorporated by reference). Research considering epidemiology results have also suggested that such orientation differences may be a key factor in the discrepancies between some reported results (e.g., Blackman & Most, Bioelectromagnetics 14: 413–431, 1990; Bowman et al., Bioelectromagnetics 16: 48–59, 1994; Liboff & McLeod, Bioelectromagnetics 16: 227–230, 1995). These results suggest that in all ELF EMF tests, regardless of the system being studied, control of the relative orientation between the ac (typically applied) and AC (typically ambient geomagnetic field) is essential, particularly to facilitate independent replication studies, to document exposure-response relationships, and to aid in further understanding of mechanisms of interaction.

Experimental Confirmation of IPR Model Bandwidth Hypothesis

As noted above, the IPR model hypothesized a characteristic field-induced biological response under exposure conditions that established critical ion resonances. The cell response for 45 Hz exposures agreed with the IPR model predictions under exposure conditions that allowed resonance for a number of ions, as characterized by an $R^2$ of 0.945 for 66 distinct data points representing different AC magnetic field exposure over the firs predicted U-shaped dip and an $R^2$ of 0.85 for 120 distinct data points extended over a total of three predicted cycles. PC-12 responses in off-resonance exposure conditions for comparable AC field exposures showed no change from control (unexposed) responses, also as predicted by the IPR model. Recent work by Trillo et al., Bioelectromagnetics 17: 10–20 (1996), demonstrated that PC-12 cells show an IPR-model-predicted response underexposure conditions designed to isolate the resonance to a single ion (hydrogen). Because hydrogen's charge-to-mass ratio is much larger than any other biologically significant ion, it provides a unique test case by which a single ionic bandwidth can be clearly measured.

The model development assumed, as a first approximation, that the actual resonant bandwidth for any ion could be estimated at ±10% ionic bandwidth using 45 Hz as the center frequency, 42.5 and 47.5 Hz as near resonance, and 40 and 50 Hz as frequencies bounding the assumed ±10% resonance bandwidth. The test measured cell response for each specific combination of frequency and DC and AC magnetic field flux densities compared to the response of unexposed controls. Six different AC flux densities were tested, chosen near the maximum response predicted by the IPR model, and each test was repeated three times.

Primed PC-12 cells were incubated with 5 ng/ml nerve growth factor for 24 hours. The cells were exposed using Helmholtz coils in a $CO_2$ incubator generated DC and sinusoidal AC magnetic fields. Exposed cells/clusters with neurites longer than one cell diameter were scored as positive and compared against results of unexposed cells (controls) with and without nerve growth factor.

The results obtained at 45 Hz replicated the results obtained independently by Trill et al., showing the characteristic on-resonance form under hydrogen resonance. The 42.5 and 47.5 Hz results demonstrated identical slightly off-resonance responses, while the 40 and 50 Hz results displayed near control or off-resonance responses. These results directly agree with IPR model predictions and validate the assumed ±10% bandwidth for the hydrogen ion both in magnitude and symmetry of response.

Comparison of Theoretical Models for Magnetic Field Interactions with Biological Systems PC-12 cells primed with nerve growth factor and exposed to specific combinations of parallel DC 29.7 and 366 mG and 45 Hz AC [34–1416 mG(rms)] magnetic fields showed distinct reductions in neurite formation over an extended set of variations in critical experimental variables. Earlier, these results were reported consistent with the predictions of the ion parametric resonance model. Here, we examine the consistency of the data with predictions of the ion cyclotron resonance model and two versions of the Lednev ion cyclotron resonance model.

Each model, ICR, Lednev, and IPR, requires parallel AC and DC magnetic fields and identified ion resonance in terms of the relation between the ion charge-to-mass ratio and the ratio of the DC field strength to the AC frequency. The Lednev model originally attempted to augment the ICR theory, as applied to biological systems, with a model originally designed for atomic spectroscopy. It differs from the IPR model in the treatment of the AC field modulation of the energy levels split by the DC field. This results in an additional factor of 2 in the argument for the Bessel function in the IPR model. Both the Lednev and IPR models differ from the ICR model in their definition of harmonics. In addition, the Lednev model focuses exclusively on calcium ions (with the possible inclusion of magnesium where it replaces calcium), where the IPR model considers any ion that might interact in its unhydrated form with a biological substrate to produce an observable result. Additional consideration is given to a model variation suggested by Lednev that uses the square of the Bessel function term.

The degree of fit was compared among the predictions of each model and the set of 120 distinct data points obtained for PC-12 cells while tuning the external magnetic fields according to the IPR model for multiple ion and single ion resonances.

The ICR model was found not to provide guidance to predict a response as a function of AC flux densities except to indicate that the maximal response should occur when the AC flux density is equal to the DC flux density, without indicating the appropriate AC metric (rms, peak, or peak-to-peak). Data were examined using each of these metrics to determine whether the maximum cell response occurred at the ratio AC/DC =1. Marginal agreement was found with the ICR model. The published form of the Lednev model does not predict the neurite outgrowth reductions observed as a function of the magnetic field variables. The predictions of the modified Lednev model, which uses a squared form of the Bessel function, also do not fit the data well. The confinement of the original and modified Lednev models strictly to calcium and magnesium ions precludes analysis of the model's fit to data obtained with magnetic field conditions tuned only for hydrogen ion resonance.

Compared with the predictions of the Lednev and ICR model, the predictions of the IPR model showed significantly better agreement with experimental data for PC-12 cells exposed to parallel AC and DC magnetic fields over a wide range of variation in each of three critical experimental variables. It was demonstrated that the IPR model provided significantly better guidance for designing experimental tests than either the Lednev of ICR models.

Frequency-Dependent Interference by Magnetic Fields of Nerve Growth Factor-Induced Neurite Outgrowth in PC-12 Cells Blackman et al., in *Bioelectromagnetics* 16: 387–395 (1995), the entire contents of which are hereby incorporated by reference, reported on the frequency dependence of the intensity-dependent reduction in nerve growth factor stimulation of neurite outgrowth in PC-12 cells over the 15–70 Hz range at 5 Hz intervals.

Primed PC-12 cells were plated in collagen-coated, 60 mm plastic petri dishes with or without 5 ng/ml nerve growth factor and were exposed to sinusoidal magnetic fields for 22 hours in a $CO_2$ incubator at 37° C. One 1000-turn coil, 20 cm in diameter, generated vertically oriented magnetic fields. The dishes were stacked on the center axis of the coil to provide a range of intensities between 3.5 and 9.0 $\mu$T(rms). The flux density of the ambient DC magnetic field was 37 $\mu$T vertical and 19 $\mu$T horizontal. The assay consisted of counting over 100 cells in the central portion (radius $\leq$0.3 cm) of each dish and scoring cells positive for neurite outgrowth. Sham exposure of cells treated identically with nerve growth factor demonstrated no difference in the percentage of cells with neurite outgrowth between exposed and magnetically shielded locations within the incubator. Analysis of variance demonstrated flux density-dependent reductions in nerve growth factor-stimulated neurite outgrowth over the 35–70 Hz frequency range, whereas frequencies between 15 Hz and 30 Hz produced no obvious reduction. The results also demonstrated a relative maximal sensitivity of cells at 40 Hz with a possible additional sensitivity region at or above 70 Hz. These findings suggest a biological influence of perpendicular AC/DC magnetic fields different from those identified by the ion parametric resonance model, which uses strictly parallel AC/DC fields.

As is well understood by those skilled in the art, different chemical or biological outcomes can be expected to exhibit different sensitivities to various ions and to various ways of affecting these ions. Using the techniques described herein, one can establish more clearly which ions and oxidation states are relevant and identifiable with this technique for a particular chemical or biological system.

The critical influence ions have on the structure and function of biological molecules was recently highlighted in reviews of the emerging area of bioinorganic chemistry (Lippard, 1993; Karlin, 1993; Pyle, 1993; O'Halloran, 1993; Abrams and Murrer, 1993; Regan, 1993). These reviews support the hypothesis that the fit of the IPR model to the experimental data may consider one or all of the n=1 ions, magnesium, vanadium, and manganese; the n=12 ion, hydrogen, as involved in the field-induced inhibition of neurite outgrowth.

The influence of ions involved in neurite outgrowth or other biological/chemical changes may involve at least one or more other critical biochemical steps. It is possible that some of the molecular-level actions could oppose each other so that observed biological responses, in contrast to molecular-level responses, may in some instances be small because of potential offsetting influences of different ions. For example, the analysis below suggests that lithium may play a minor opposition role vs. that of the other ions. Because, under the exposure condition selected from these tests, the frequency index of 1 is common to magnesium, vanadium, and manganese, it is more difficult to determine directly exactly which molecular processes, e.g., enzyme reactions, are affected in the exposures. Nevertheless, examination of exact conditions for predicted null responses for each of these n=1 ions at larger values of $B_{ac}$ (or smaller values of $f_{ac}$ and $B_{dc}$) can provide the information to select the affected ion(s) and thus ultimately provide identification of the molecular processes involved.

Assay Procedures

After exposure, the cells were assayed in a blinded fashion from pseudo-random (i.e., non-overlapping) areas near the center of each dish. The neurite outgrowth assays determined the number of cells either with a neurite length greater than the cell body or with neurites containing either a branch or a growth cone (these accounted for approximately 5% of the total cells scored positive) to create a raw cell scoring. All cells were counted within each microscopic field, and at least 200 cells per dish were assayed.

However, each set of primed cells can produce a slightly different response to nerve growth factor. Corrections were made for differences between sets of primed cells through the responses shown by magnetically shielded controls specific to each experiment to make the measured response between test runs comparable, as described infra. These assay procedures for neurite outgrowth are well established (cf. Greene and Tischler, 1976; Greene, 1977; Blackman et al., 1993, 1994; Rukenstein and Greene, 1983).

Experimental Results

In Test 1 shown in Table 2, the coil was energized with 3.9 mG(rms) to create a flux density range over which the IPR model (for n=1) predicts a monotonically decreasing probability of energy transitions between states, seen here as increased inhibition of neurite outgrowth, as the AC flux density, $B_{ac}$, increases. The AC magnetic field was colinear with the DC magnetic field of 366 mG. The experimentally observed decline in neurite outgrowth with increasing $B_{ac}$ between 77 and 200 mG(rms) [108–283 mG(pk)], shown in FIG. 1, is consistent with the predictions of the IPR model. It is noteworthy that each repetition of this exposure demonstrated the same response form. The results for each run are shown to emphasize the actual ranges of the data.

Figure 2:
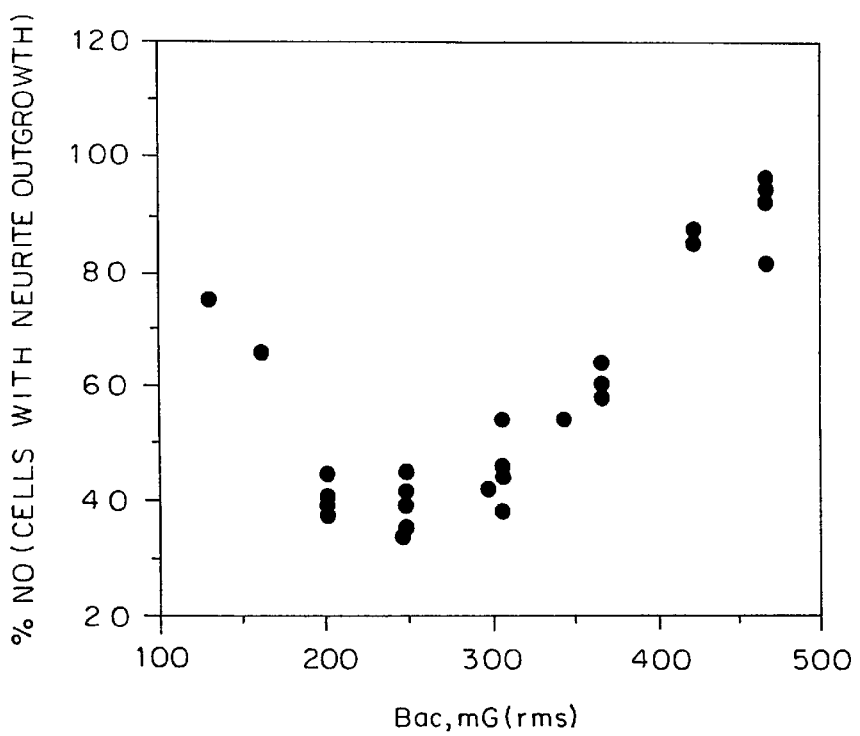
FIG. 2 shows the results of Test 2 for reduced effectiveness of 45 Hz sinusoidal magnetic fields between 200 and 468 mG(rms) [284–662 mG(pk)] to inhibit neurite outgrowth stimulated by nerve growth factor in PC-12 cells.

Four runs of Test 2 were conducted with the coil energized at 8.27 mG(rms). Again, the AC magnetic field was colinear with the DC magnetic field of 366 mG. As shown in FIG. 2, the experimental results of $B_{ac}$ from 200 to 468 mG(rms) [284–662 mG(pk)] are consistent with the predictions of the IPR model using the peak value of $B_{ac}$. Again, repeat tests demonstrated the consistency of this response form. A fifth run was conducted at 45 Hz under conditions [$B_{ac}$ range of 132–344 mG(rms), or 186–486 mG(pk), generated by energizing the coil with 6.7 mG(rms)] that overlapped those in tests 1 and 2 to verify continuity of the test results across the range of AC flux densities. The results of Test 2 demonstrate the reduced effectiveness of 45 Hz sinusoidal magnetic fields between 200 and 468 mG(rms) to inhibit neurite outgrowth stimulated by nerve growth factor in PC-12 cells.

Figure 3:
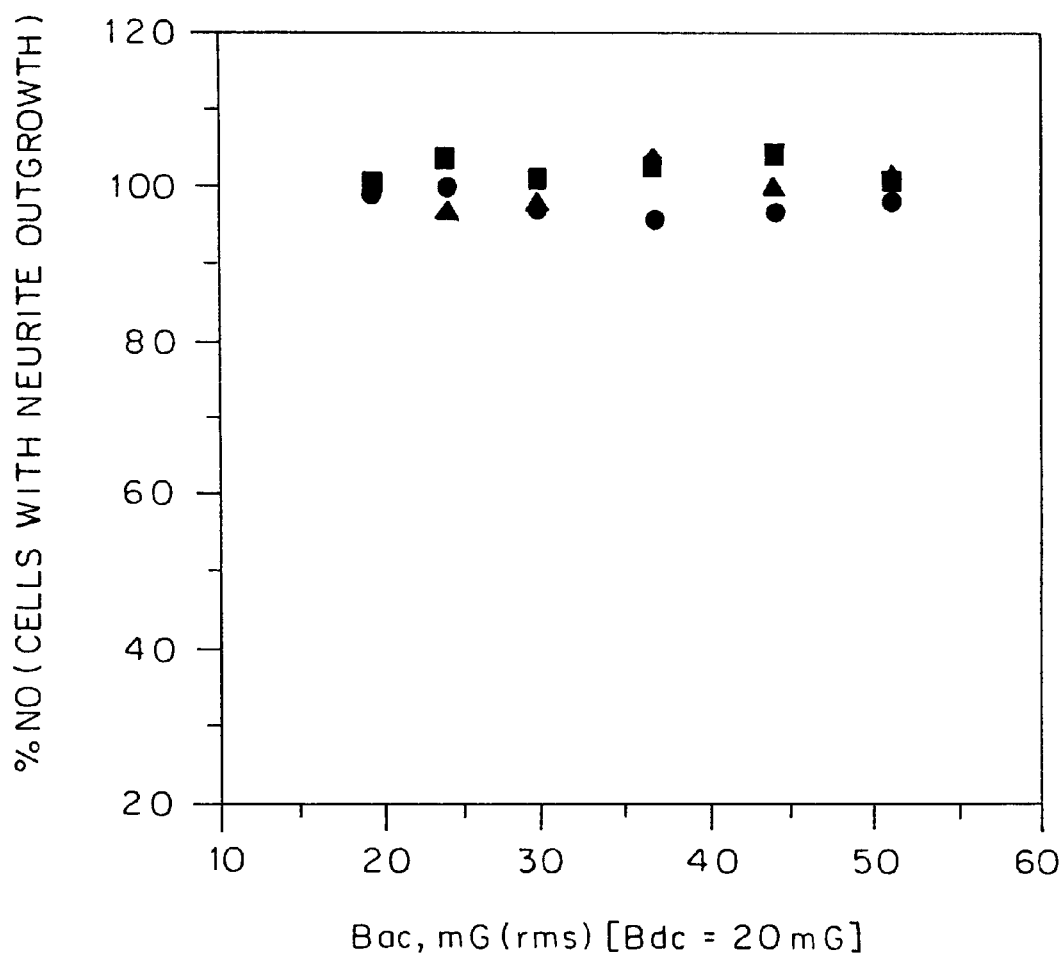
FIG. 3 shows the results of Test 3 for the response of nerve growth factor-stimulated PC-12 cells to 45 Hz, sinusoidal magnetic fields under non-resonance conditions.

Test 3 examined the response of cells over a $B_{ac}/B_{dc}$ range of 0.54–1.41. The previous tests showed a distinctive U-shaped inhibition of neurite outgrowth as $B_{ac}$ increased in intensity, which is consistent with IPR model predictions. However, in Test 3, $B_{dc}$ was set to 20 mG to create conditions well "of resonance" for all biologically relevant ions. As a check, it can be noted that the limiting case of hydrogen (n=0.676) is well off resonance under Test 3 conditions. Because no ion is near resonance, the IPR model predicts a constant response across the AC flux density range chosen for this test [7.9–21 mG(rms), 11–29 mG(pk), 0.405 mG(rms) in the coil]. This prediction was confirmed by the empirical data shown in FIG. 3, replicated three different times. As noted above, under resonance conditions, this range of $B_{ac}/B_{dc}$ produced a U-shaped inhibition response, as shown in FIG. 2.

The final test of the series evaluated whether the on-resonance results observed for Tests 1 and 2 can be obtained at a different frequency. Test 4 examined the use of 25 Hz AC fields and $B_{dc}$=203 mG to give on-resonance conditions identical to those in the 45 Hz cases, i.e., Tests 1 and 2. In this test, the coils were energized at 3.2 mG(rms) to create a range of $B_{ac}$ comparable to that used in Tests 1 and 2. This test also examined the importance of the Bessel function argument as the correct exposure metric. If the change in $B_{dc}$ and $f_{ac}$ were insignificant except for ion selection, then the exposure range would be comparable to that of Test 1 and the response would be a monotonically declining percentage of neurite outgrowth with increasing $B_{ac}$. If, however, the argument of the Bessel function were the important exposure variable, then the result should be a U shape characteristic of the combination of test cases 1 and 2.

Figure 4A:
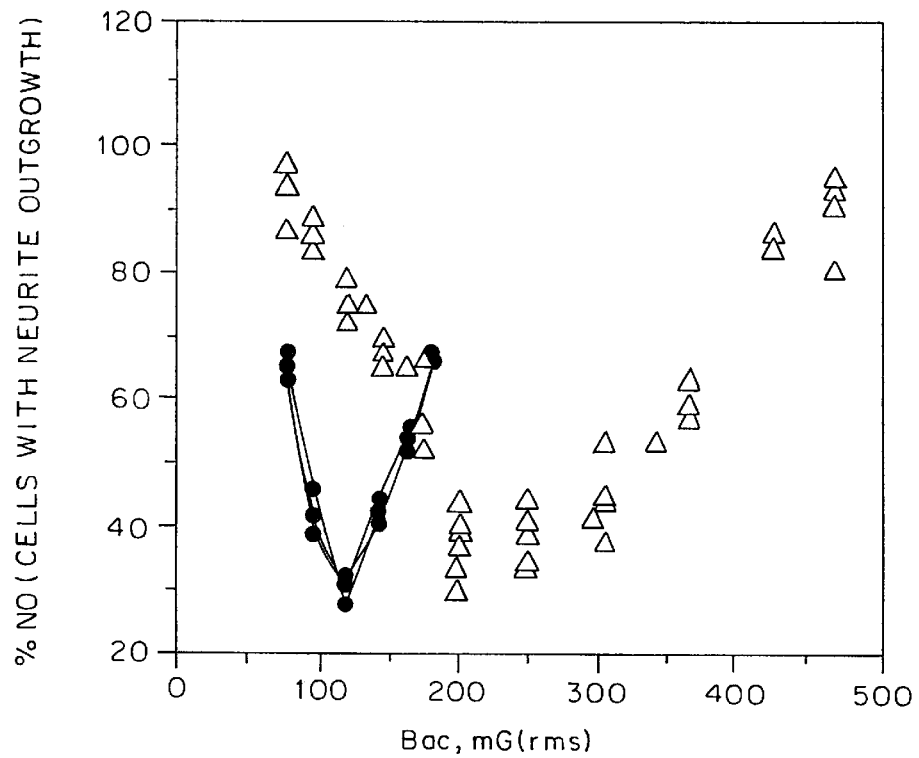
FIG. 4a shows a comparison of neurite outgrowth in cells stimulated by nerve growth factor and exposed to sinusoidal magnetic fields under resonance conditions by AC exposure frequency (45 Hz vs. 25 Hz where the 25 Hz responses are connected by lines) but plotted without regard for the different $B_{dc}$ flux densities that are present in the 45 Hz v. 25 Hz cases.
Figure 4B:
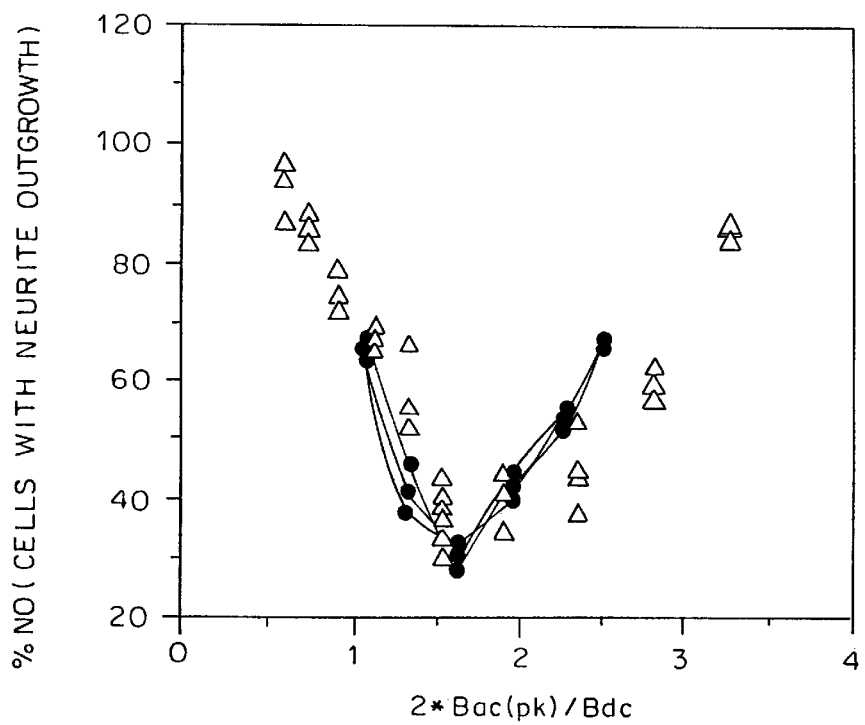
FIG. 4b shows the results from each run when the different $B_{dc}$ flux densities are included as part of the independent variable (plotted on the horizontal axis) to indicate the IPR model predicted Bessel function argument.

FIG. 4 shows the results of three repetitions of this test in comparison to the combined results of Tests 1 and 2. FIG. 4a plots the data in terms of the AC flux density of $B_{ac}$ (rms), whereas FIG. 4b plots each response as a function of 2.$B_{ac}$ (pk)/$B_{dc}$, as suggested by the IPR model. These results demonstrate essentially identical cellular responses as a function of exposure when compared in terms of the Bessel function argument, 2.$B_{ac}$ (pk)/$B_{dc}$, indicated by the IPR model, but not when $B_{ac}$ is used alone as the common point of reference. This result highlights the importance of using the IPR model identified form of Bessel function argument when identifying and comparing results under different exposure conditions.

Fit of IPR Model Predictions to Experimental Data

Figure 5A:
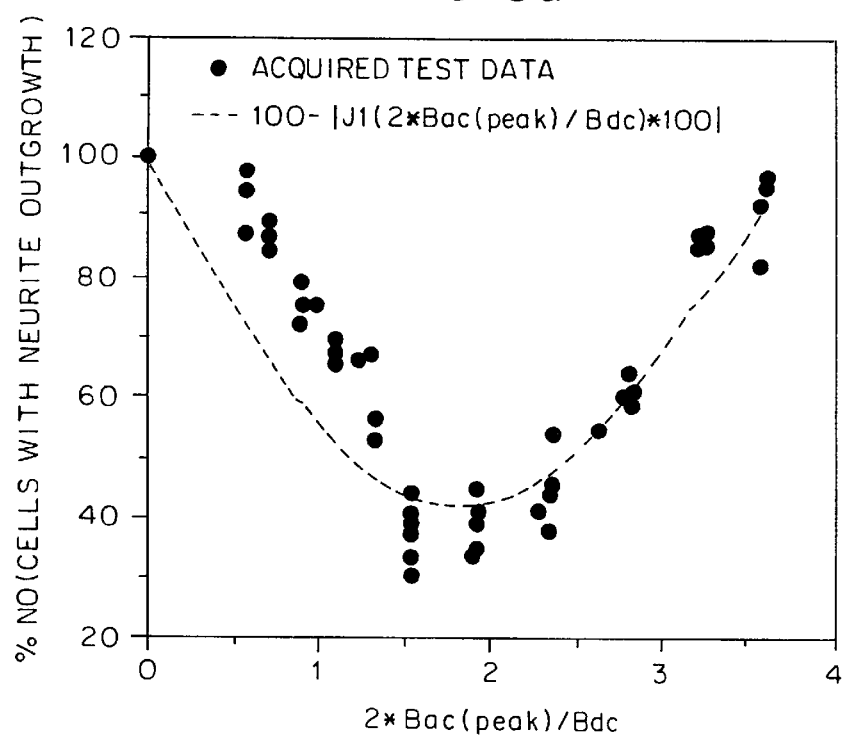
FIG. 5a shows the general fit of n=1 prediction of IPR model to data acquired from Tests 1, 2 and 4.
Figure 5B:
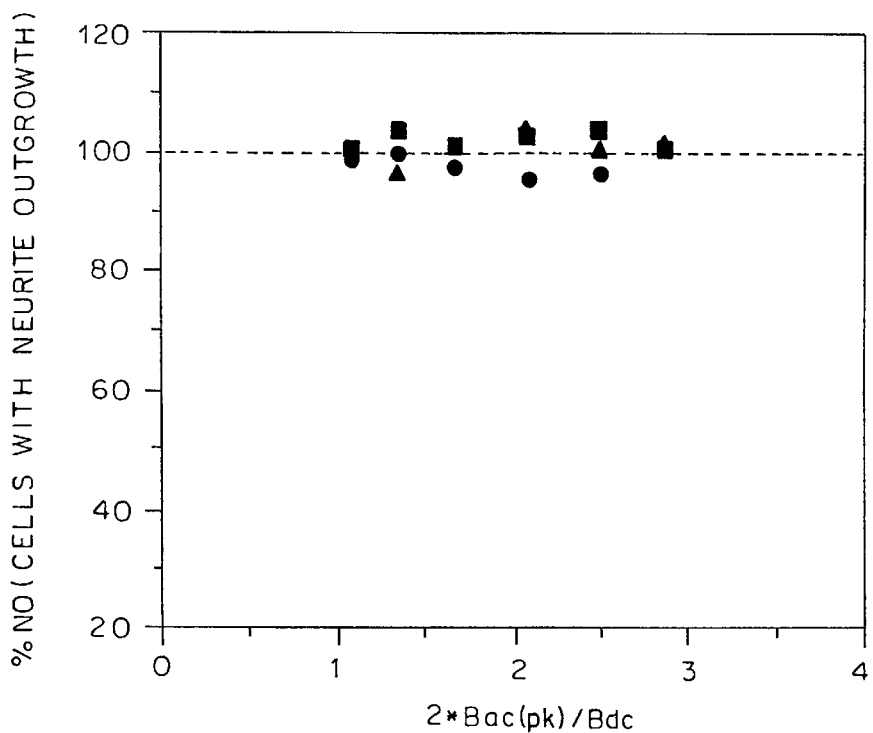
FIG. 5b shows the near constant results across the range of $B_{ac}$ for off-resonance conditions, Test 3.

The experimental data show consistency between runs and follow the general form of response predicted by the IPR model, as demonstrated in FIG. 5. FIG. 5a shows the combined results of Tests 1 and 2 plotted against an arbitrary fit of the n=1 prediction by the IPR mathematical model. FIG. 5b demonstrates how the results of the off-resonance test (Test 3) are very nearly constant across the range of $B_{ac}$ tested. Again, the experimental data followed very closely the IPR mathematical model predictions.

It has been demonstrated above that the results of neurite outgrowth assays for PC-12 cells exposed to magnetic fields are consistent with the distinctly nonlinear and nonobvious predictions of the IPR mathematical model. The IPR mathematical model indicates how $B_{dc}$ and the AC frequency select responses from ions based on their charge to mass ratio. The model is unique because it is the first mathematical model to predict specific, distinct responses based on the experimentally controllable variables $B_{ac}$, $B_{dc}$ and $f_{ac}$. The experimental results show that full characterization of the independent variables, $B_{ac}$, $B_{dc}$ and AC frequency, is essential.

Figure 6:
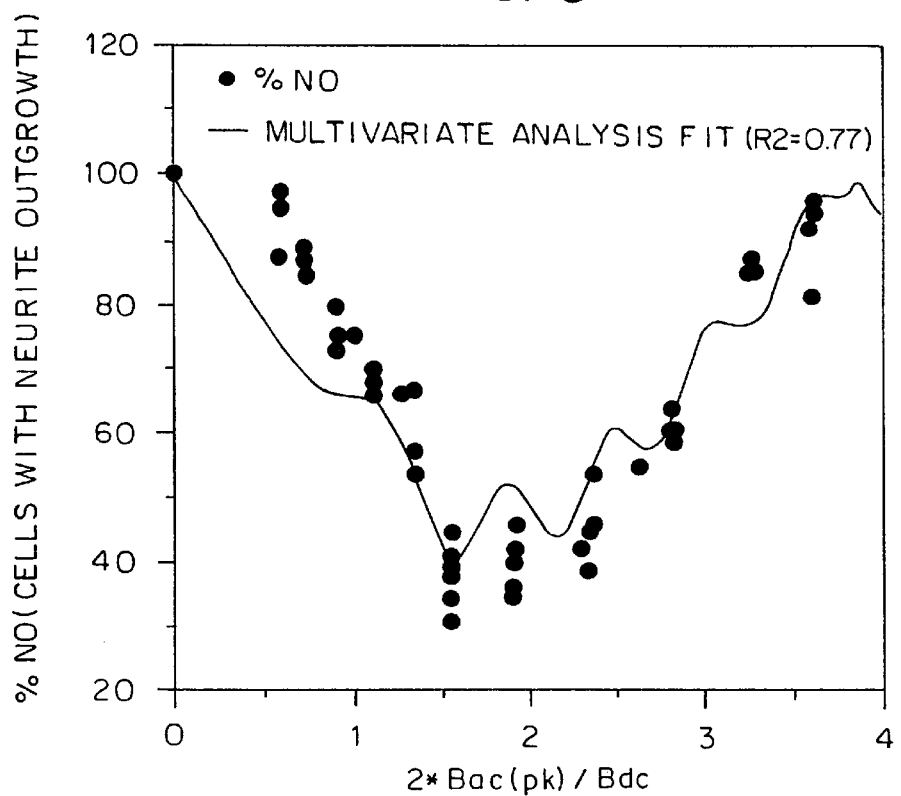
FIG. 6 shows a best fit to data using the simplest interpretation of the IPR model: a weighted sum of Bessel function responses selected by ions at or very near resonance.

FIG. 5a demonstrates the fit of the data with the predictions of the IPR mathematical model using just the Bessel function for n=1 ions. Although the fit was reasonably good, the fit improved when the potential contributions from the n=2 and 12 ions, predicted by the IPR mathematical model to be resonant under the current exposure conditions, were included ($R^2$=0.77) (see FIG. 6).

Under the particular set of exposure conditions tested, a distinct, repeatable influence was observed on neurite outgrowth in PC-12 cells as a function in increasing $B_{ac}$. The response form was consistent with the predictions of the IPR model, with a predominant effect by n=1 ions (consisting of any or all of Mg, Mn, V). One of the crucial distinctions between the IPR model and its predecessors is the extension of proposed influence to a variety of ions beyond calcium and magnesium that have shown biological significance. It was discovered that the biological/chemical system itself determines whether any particular ion is sufficiently near resonance to create a change in the selected observable (in this case, neurite development). The exposure conditions created n=1 for several biologically significant ions, including $Mn^{4+}$, $V^{4+}$, and $Mg^{2+}$, in addition to the n=2 ions previously identified. This result is consistent with the dominance of an $Mg^{2+}$ion-based effect under resonance conditions recognized by all three models. More compelling evidence supporting the possible involvement of both $Mg^{2+}$ and $Mn^{4+}$ resonances in the neurite outgrowth response of PC-12 cells to prescribed combinations of $B_{ac}$, $f_{ac}$ and $B_{dc}$ comes from reports by Landreth et la (1990) and Sano (1992), cited by Blackman et al. (1994, p. 243), identifying both magnesium and manganese as cofactors in the phosphorylation of microtubule-associated proteins in neurites that are induced by nerve growth factor.

The IPR mathematical model suggests that, as a first approximation, each ion functions independently to produce the observed response and that the overall response will be a linear, weighted sum of the individual response functions, unless there is evidence to the contrary. To examine how closely the experimental data for Tests 1 and 2 were predicted by the IPR mathematical model, the normalized data were fit using the iterative multivariate secant method to determine least squares estimates of the coefficients ($K_{2,x}$) of the Bessel functions in the IPR-predicted response form corresponding to frequency indices of 1, 2 and 12:

$$\text{Fit}=100-|K_{2,1} \times J_1(2B_{ac}/B_{dc}) + K_{2,2} \times J(2 \times 2B_{ac}/B_{dc}) + K_{2,12} \times J_{12}(12 \times 2B_{ac}/B_{dc})| \qquad (4)$$

An absolute value was incorporated in the data fit because it was believed that the NGF-induced neurite outgrowth process in PC-12 cells is maximally efficient without any perturbation from fields. Under parallel AC and DC magnetic field exposure, any perturbation away from optimum response would make the induction of neurite outgrowth less efficient regardless of the molecular level direction of the perturbation or relative efficiency. This situation is not necessarily universal, as demonstrated by Ross (1990), whose assay of rabbit ligament fibroblasts showed both inhibition and proliferation of growth, depending on the exposure conditions.

Figure 7:
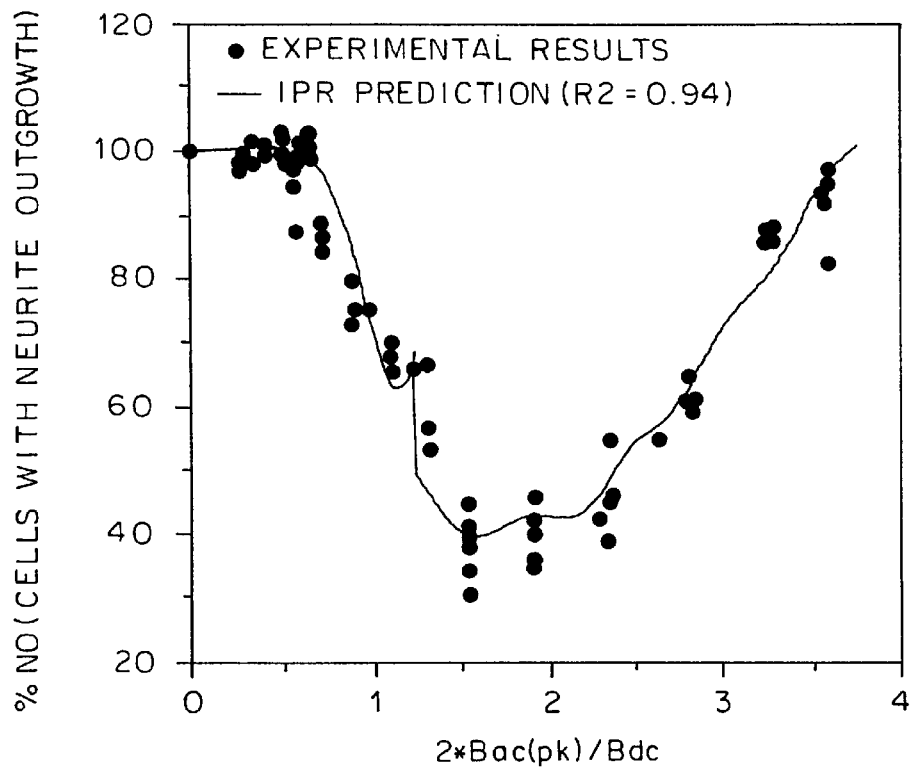
FIG. 7 shows an improved fit when the response associated with the hydrogen ion is considered exclusively for the low $B_{ac}$ response, with a conversion to a weighted sum of Bessel functions at a mathematically determined optimal conversion point. This result suggested a special role for the hydrogen ion, that was later confirmed by other experimentalists (Trillo et al., 1994). In that work, the conversion point identified here also showed a critical distinction in the data.

The IPR mathematical model is based upon independent contributions from ions at resonance, unless there is evidence to the contrary. At low exposure values, the PC-12 cells displayed substantially less actual inhibition in neurite outgrowth than indicated by the model composed of the weighted sum of IPR mathematical model selected Bessel functions. This was confirmed by an additional set of tests at lower $B_{ac}$ values. The data in this region show a close fit with the IPR mathematical model predictions for hydrogen alone (n=12). Since hydrogen is an ion with known influence on chemical reactions through their sensitivity to pH, it was hypothesized that at lower AC field intensities, hydrogen provides sufficient stability to the biochemical structure so that the predicted magnetic field interactions with other ions would not be observed at the level of the cell response. At higher AC magnetic field intensities there is sufficient destabilization of the biochemical molecule through field interaction with hydrogen to observe the predicted magnetic field influence on other ions complexed with that molecule. The best fit of the IPR mathematical model to the experimental data (see FIG. 7) assumed an hypothesis that hydrogen has a different role, acting as a trigger ion at low field values for the PC-12 cell assay ($R^2$=0.94). This is not an unreasonable hypothesis, since pH plays a critical role in biological functions. If some portion of the available hydrogen in the system, meeting the criteria for the IPR mathematical model, is associated with stabilizing a site that is influenced by one of the other ions at resonance, the field-induced result may be as observed. Pilot studies that specifically isolated hydrogen as the resonant ion and tested the cell response against the predictions of the IPR mathematical model (Trillo et al., 1994) provide further support for this contention and demonstrates a clear influence of hydrogen on neurite outgrowth in PC-12 cells exposed to parallel AC and DC magnetic flux densities.

It is remarkable that the IPR mathematical model accounted for up to 94% of the variance in the PC-12 data, representing a biologically observable change, over a critical, limited, and relatively low intensity range of AC magnetic fields. The closeness of fit demonstrated between experimental data and theoretical predictions is excellent, particularly considering that the IPR mathematical model addresses field-induced changes at the molecular level whereas the experimental endpoint, neurite outgrowth, is the integrated response of an intact cell to field exposure for 23 hours.

The field-induced inhibition of neurite outgrowth under resonance conditions for Mn and Mg (n=1) is consistent with other previously cited studies showing a critical role for Mn and Mg in nerve cell (e.g., PC-12 cell) functions. These results support the formalism of the IPR mathematical model, including the exposure-determined frequency indices, the excellent fit of the mathematical model at all $B_{ac}$ values, the capability of the mathematical model to predict both the relative changes in inhibition for each cycle and the intensities at which the null effects occur, and the influence of hydrogen ion resonance on the biological process, a previously unsuspected important resonant interaction.

As a quick test of the responsiveness of the system, an observable quantity (such as a chemical or biochemical reaction such as a cellular signal transduction event) is approximately no different from the unexposed case when the system is exposed to parallel AC and DC magnetic fields when $2B_{ac}$ (pk)/$B_{dc}$=3.6 to 3.8 and the AC frequency is selected to establish resonance for an ion involved in the process. It is not essential to know for certain which ion is involved in the process to be controlled. Good first choices include hydrogen, magnesium, and calcium, but the method will apply to any ion in a biological or chemical system.

In most cases, one can expect the maximum deviation of the system response from the unexposed case as a result of controlled exposure to parallel AC and DC magnetic fields at $B_{ac}$ (rms)=0.64*$B_{dc}$ [or the equivalent expressions $2B_{ac}$ (pk)=1.8$B_{dc}$ or $B_{dc}$=1.57*$B_{ac}$ (rms)].

In at least one test system, a competing effect or an attenuation response was observed at this combination of fields [$B_{ac}$ (rms) =0.64*$B_{dc}$ ], but an additional set of tests at 2 point symmetrically selected around the previously predicted maximal response point confirmed the general applicability of the process of the present invention when the system response was (a) markedly different from the unexposed response and (b) the two response at these two different exposures were approximately comparable in magnitude.

Figure 8:
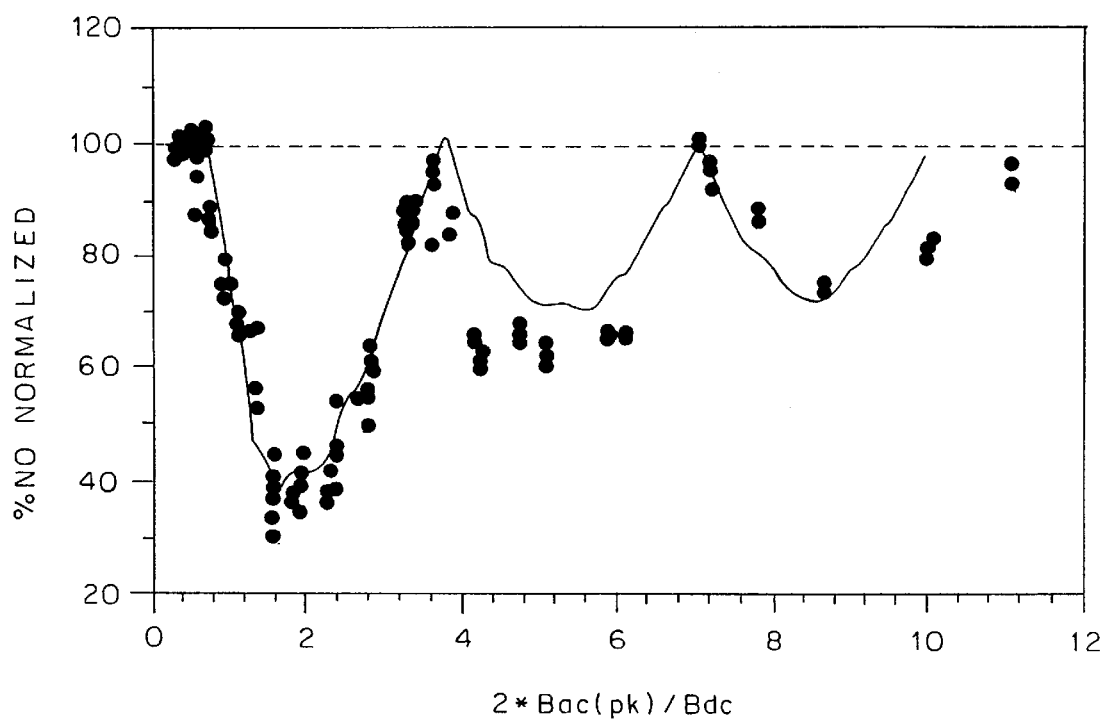
FIG. 8 demonstrates continued consistency of PC-12 cell responses with IPR model predictions under specific IPR model prescribed combinations of AC and DC magnetic fields. The IPR model fit to the data in FIG. 7 was extended to higher values of $B_{ac}$, where the results of experimental tests at those values were then plotted. This match of the data to such an unusual predicted response form is extremely unlikely to occur by chance.
Figure 9:
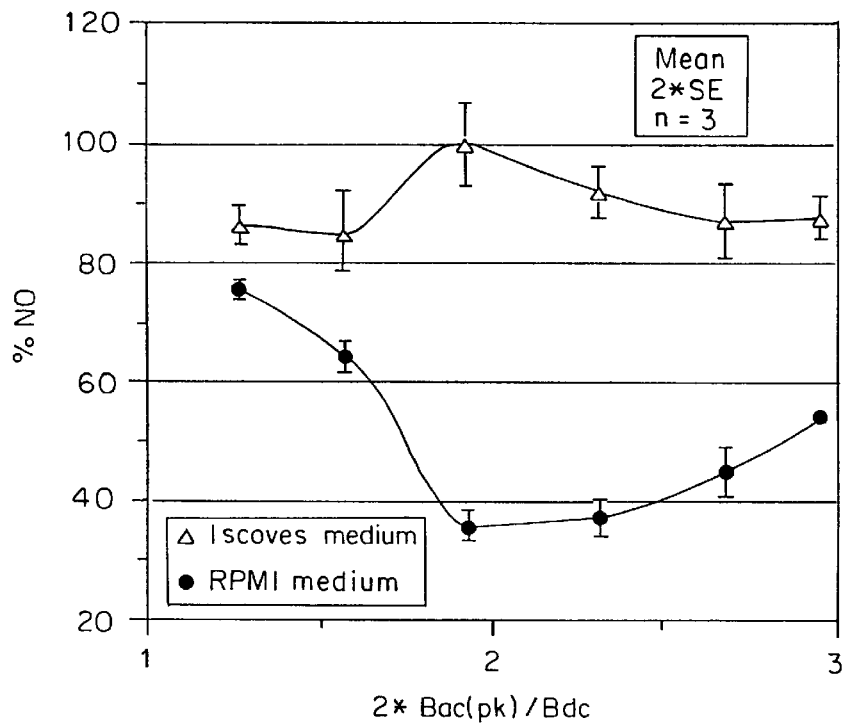
FIG. 9 shows that cells prepared in the standard medium, RPMI 1640, exhibited the IPR model anticipated response form whereas those prepared in Iscoves' medium exhibited a minimal response, nearly indistinguishable from an IPR model predicted off-resonance response form, although the magnetic field exposure conditions for each of these tests were essentially identical. This result is consistent with the effect of magnetic fields being localized to the cell plasma membrane.
Figure 10:
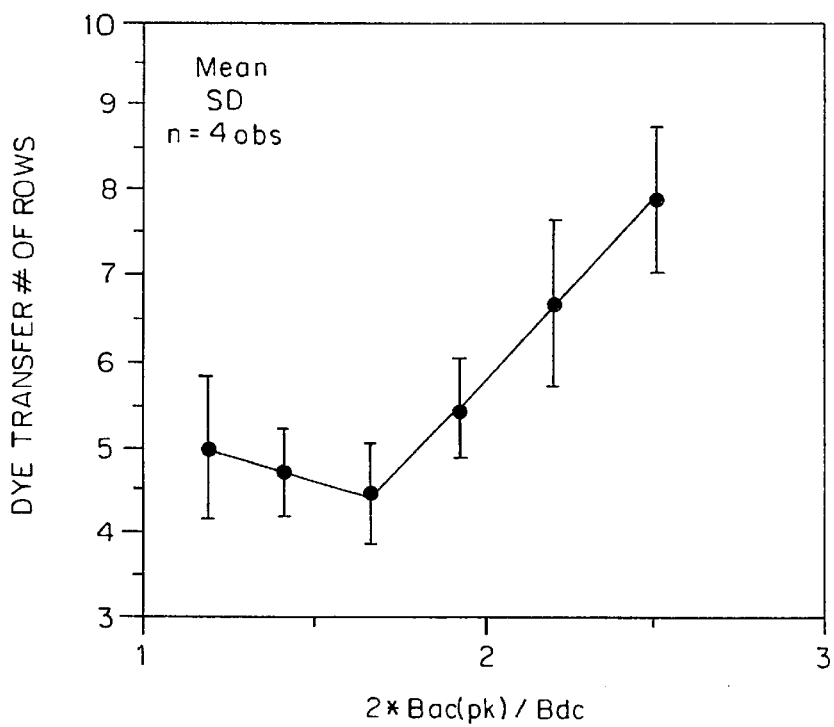
FIG. 10 demonstrates an alternate biological/chemical system response to IPR model specified conditions. Rat liver cells in culture (Clone 9) exhibit gap junctional intercellular communication by transferring a fluorescent dye away from the site of application, which is quantified by scoring the number of rows away from the application point that are stained with the dye. Under the influence of IPR exposure conditions similar to those described for neurite outgrowth in PC-12 cells, the expected U-shaped exposure response is observed. Although less detailed than the PC-12 measurements, these data show, in a preliminary way, the reasonableness of extending the IPR model to systems other than PC-12 cells.
Figure 11:
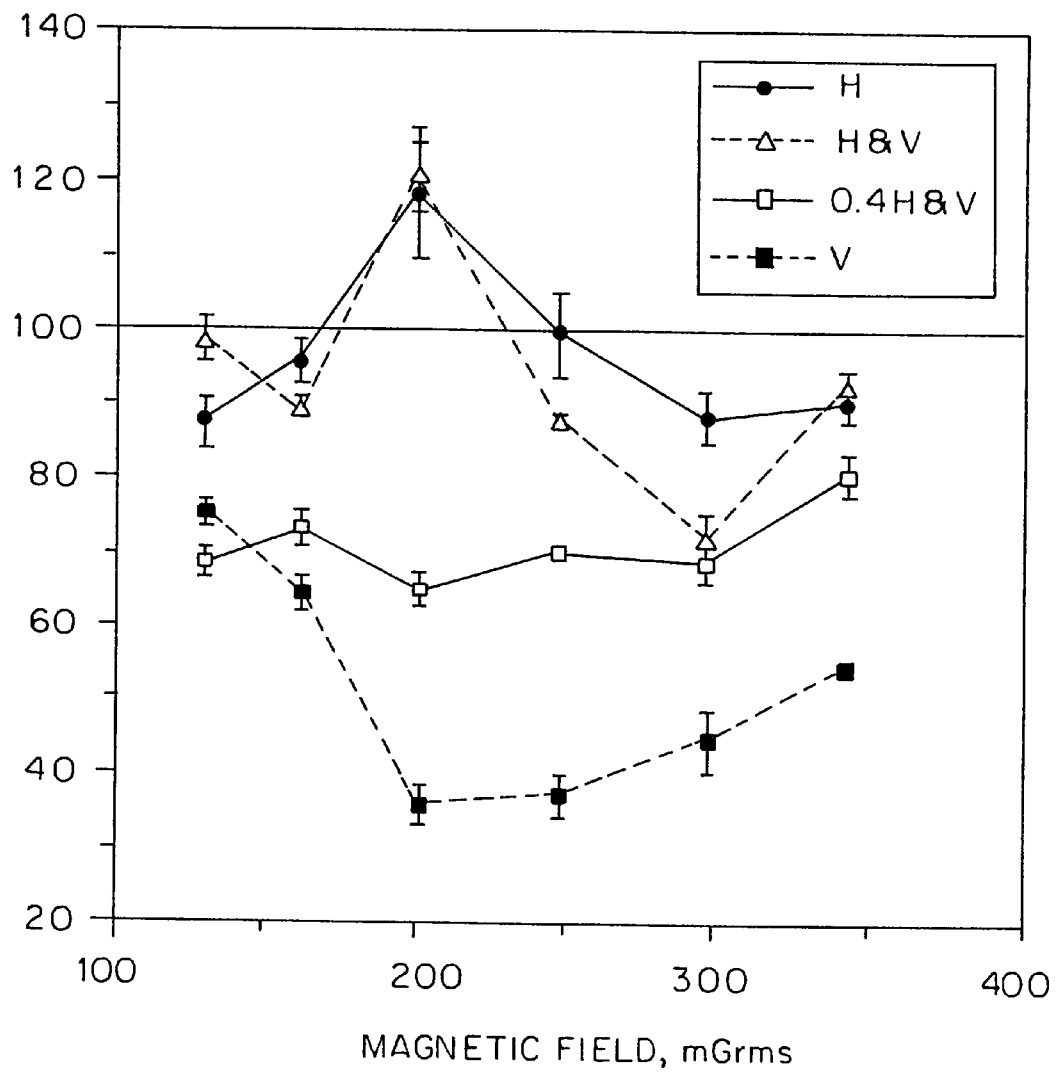
FIG. 11 shows the neurite outgrowth response of cells exposed over a field-strength range of 45 Hz AC magnetic fields under various different $B_{dc}$ orientations and flux densities. The mean and 2·SE of the percent neurite outgrowth (%NO) is plotted for four different DC magnetic field conditions. H(5 trials) is for 366 mG perpendicular, <2 mG parallel DC magnetic fields. H&V (3 trials) is for 366 mG perpendicular, 366 mG parallel DC magnetic fields. 0.4H&V (3 trials) is for 160 mG perpendicular, 366 mG parallel DC magnetic fields. V (3 trials) is for <2 mG perpendicular, 366 mG parallel DC magnetic fields. These results demonstrate that the orientation and flux density of the $B_{dc}$ relative to the $B_{ac}$ can negate parallel field resonance conditions, and even reverse the cell response for strictly perpendicular $B_{ac}/B_{dc}$ under specific exposure conditions.

In many if not all cases of ions other than hydrogen being placed under resonance, the hydrogen predicted response dominates the observed responses at lower values of $2B_{ac}$ (pk)/$B_{dc}$, and no response is seen until the hydrogen prediction begins to differ from essentially zero. When a hydrogen trigger is included (this exposure value is determined by a calculation of the hydrogen probability of transition between energy states using a frequency index for hydrogen, determined by the exposure conditions, which is more than 1), the observed changes related to resonance of these non-hydrogen ions begin to occur just at the exposure value where the change in hydrogen probability of transition between energy states reaches its predicted first maximum excursion. This is illustrated in Blackman et al., BEMS 15: 239–269 (1994), FIG. 8 on page 242 for hydrogen alone, and FIG. 9 on page 253 for hydrogen and then the other ions at resonance, the entire contents of which are hereby incorporated by reference.

Once responsiveness of a chemical or biological system (i.e., observed endpoint) is established via the minimal experimentation described above, the mathematics of the process gives a very precise method for controlling the degree of response of a system to magnetic fields imposed on that system. Conversely, to obtain a particular percentage of maximum response, the model provides precisely what combination of magnetic fields should be used to obtain this percentage of the maximum response.

For example:

Degree of response compared to maximum: 60% 70%

Requires $2B_{ac}$ [pk]/$B_{dc}$=0.75 or 2.96 0.9 or 2.82

The non-linearity of the IPR model-predicted effect and the actual response of tested systems makes it impossible to produce an effect without knowledge of the IPR. Non-linearity in this case means that more magnetic field does not necessarily produce more of an effect, so that the natural intuition of a scientist to use higher AC field flux densities would bias against producing an effect.

The present invention identifies values of $2B_{ac}$ [pk]/$B_{dc}$ that would lead to no effects in a cyclic fashion, and that the effect diminishes in maximum value for additional cycles of effect until there is no effect at high values of $2B_{ac}$ [pk]/$B_{dc}$. The process of the present invention gives precisely the amount by which the biological effect will be moderated or controlled from the maximal effect at $2B_{ac}$ [pk]/$B_{dc}$=1.8 exposure.

The magnetic field influence of parallel AC and DC magnetic fields can be reversed by changing the orientation of the fields from parallel to perpendicular. This cannot be determined without using the IPR model. Reversal is particularly effective at the maximal parallel field effect point, cf. Blackman et al., *Biochem, Biophys. Res. Communications* 220: 807–811 (1996).

The effect of the parallel magnetic fields can be cancelled by changing the AC frequency by 10% of its value to take the system off resonance. For example, by changing the AC frequency from 45 Hz to 40 Hz or to 50 Hz, the system is taken off resonance and the effect of the parallel magnetic fields is cancelled.

Additional control of the parallel magnetic field effect is obtained by slightly varying the AC frequency. For example, the response at 42.5 Hz is 60% of that of the response at 45 Hz. For bandwidth data using neurite outgrowth experiments as described above, the mean value at 45 Hz is 55% neurite outgrowth (which is a 45% change) and and 42.5 and 47.5 Hz, there is 72.5% neurite outgrowth, which is a 27.5% change. The relative difference is 27.4/45=0.61, so the the response at 42.5 and 47.5 Hz is approximately 60% of the maximum value for hydrogen. Where the maximum is less than for other ions, the difference could be even greater, i.e., 40–50% of maximum.

In general, the IPR model of the present invention can be used to examine or to treat chemical and biological systems as follows:

I. Initial approach to select ionic resonance conditions

First of all, one must determine the ion or set of ions to be stimulated, either from previous reports of ions responding under resonance or from special knowledge of ionic cofactors involved with a particular process being studied. Alternatively, one can use the process to determine if a particular ion or group of ions is playing a role in a chemical or biological system in accordance with the requirements of the IPR model. For example, good first choices for ions to set at resonance include hydrogen, magnesium, or calcium; however, the method is applicable to any ion known to be active in a biological system. Each of the ions listed in Table 1 has some published support for potential biological activity.

If one does not known what ions are involved in the particular chemical or biological activity that is to be changed, the default exposure conditions should be set to resonant hydrogen ions at a frequency index of 1(n=1), with the caveat listed below for selection of $2B_{ac}$ [pk]/$B_{dc}$. Liboff, in U.S. Pat. No. 5,040,050, discloses that among these ions are potassium ions, magnesium ions, sodium ions, chloride ions, phosphate ions, sulfate ions, carbonate ions, bicarbonate ions and the like, as well as various ions formed by the dissociation of amino acids, proteins, sugars, nucleotides, and enzymes.

II. Establish DC flux density and AC frequency

The resonance equations of the present invention are used to determine DC flux density ($B_{dc}$) and frequency to give an integer frequency index. It should be noted that the response form prediction becomes generally more complicated for higher frequency indices, so it is preferable to try to tune for lower frequency indices. The frequency index is, by definition, the order of the Bessel function describing the predicted response form. If one wishes to resonate several ions, one can use the resonance equation to determine the conditions that will produce frequency indices next to a whole number (at least within 10% of resonance) simultaneously for all ions of interest. When attempting to simultaneously resonate ions at different frequency indices, there is another equation to be used to determine the AC flux density ($B_{ac}$ [pk]) that will give the optimum transition probabilities for ions at each integer frequency index. It may be that the ions selected are not able to be stimulated simultaneously because the equation describing the probability of transition between energy states shows that the conditions produce transition probabilities that are too close to non-resonance levels to provide a large enough effect to be observed with a given ion. For large organic molecules exhibiting a charge, the charge to mass ratio will be low because of the high mass of the molecule. This means that the $B_{dc}$ will be larger than for smaller molecules.

The relationship of the DC flux density and the AC frequency to produce integer frequency indices for ionic tuning is the reciprocal of the relationship described by Liboff. In other words, the combination of DC flux densities and the AC frequencies used by the IPR model of the present invention do not overlap with the combination of these entities when used in the Liboff model. Thus, the combinations used in the present invention are mutually exclusive of those used in the Liboff model. The only overlap in the two approaches is the single point at the fundamental frequency/DC flux density value to give a frequency index of 1. However, it should be noted that the harmonics of the the IPR model are the mathematic inverse of the Liboff harmonics.

III. Requirement for parallel and not perpendicular AC/DC.

Within the space that will contain the sample to be treated, the AC and DC magnetic fields must be parallel, with only a small fraction of the flux densities of the DC and AC fields perpendicular to each other. For example, if the $B_{dc}$ is 366 mG parallel to the AC field, then the $B_{dc}$ component perpendicular to the AC fields should be below 2 mG to optimize the application of the IPR model. It is possible for the flux density of the perpendicular $B_{dc}$ component to be 3% of the parallel component and not alter predictions of IPR model, while at 24% of the parallel component the predictions would be altered.

IV. Influence of AC flux density

The equations describing the probability of ionic transition between energy states for ions at resonance (i.e., resonance being those conditions of $B_{dc}$ and frequency that give frequency indices at or near (i.e., within about 10%) of integer values) to determine the degree of ionic energy level transition desired. If the treated system is placed in a uniform $B_{dc}$ and $B_{ac}$pk, the entire system will be stimulated in the same manner and to the same degree. Two fundamental exposures are tested for onresonance conditions, $2B_{ac}$ [pk]/$B_{dc}$=1.8 and 3.6–3.8 to determine if exposure under these conditions can effect a change in the treated system response. If an effect is obtained at 1.78 but no effect or a much attenuated effect is obtained at 3.6–3.8, one then uses the probability of the ionic transition equation to select the degree of effect and multiple resonance tuning stimulation. If no effect is obtained at $2B_{ac}$pk/$B_{dc}$=1.8, the next combination to test is $2B_{ac}$pk/$B_{dc}$=1.35 and/or $2B_{ac}$pk/$B_{dc}$=2.35–2.40. If an effect is then obtained, one can use the probability of the ionic transition equation to select the degree of effect, with the exception that can determine theoretically the observed results between $2B_{ac}$pk/$B_{dc}$=1.45 and 2.25.

V. Spatially varying flux density of AC and DC

By spatially varying either the $B_{ac}$pk or the $B_{dc}$, or both, it is possible to select, based on the equations for resonance and for ionic transition probabilities, smaller volumes of the treated system that would contain resonance exposure conditions stimulating the system to different degrees. The exposure conditions that lead to different degrees of stimulation of ionic transitions would lead to different amounts of change in the observed effects in treated system volumes.

VI. Sensitizing chemical or biological systems by stimulation with chemical or other physical agents A wide variety of (chemical) agents can be used to perturb cells from their homeostatic situation and thereby render the cells sensitive to magnetic fields of the type and conditions required by the IPR model. These agents can be natural or artificial chemicals, including growth factors such as nerve growth factor, hormones such as melatonin, chemical signaling agents such as cytokines, and toxic agents such as tamoxifen, pertussis toxin, and chloral hydrate, as well as chemotherapeutic compounds such as cytosine arabinoside.

For determining the effects of chemical agents, the agent, such as cytosine arabinoside, is administered to the subject in the customary manner. The dosage is consistent with the known effective dosage for the particular chemotherapeutic agent, although use of the IPR model permits a reduction of the standard dosage under appropriate conditions.

Chemotherapeutic agents which can be used in the practice of the present invention are those which demonstrate substantially enhanced therapeutic action in the treatment of cancer when administered in connection with selected frequencies and flux densities according to the present invention over control applications of the chemotherapeutic agent without exposure to the magnetic fields of the present invention. This can be readily determined by in vitro or in vivo animal experiments. Preferred chemotherapeutic agents for use in this aspect of the present invention include alkylating agents and nucleic acid analogs.

Physical agents can also be effective in perturbing cells from their homeostatic situation and thereby render the cells sensitive to magnetic fields of the type and conditions required by the IPR model. These agents include ionizing and non-ionizing radiation, e.g., X-rays, ultraviolet, visible, and infrared radiation, and all classes of vibrations.

Additionally, some stimulatory chemicals can cause a change in the system response that is augmented by the magnetic field exposure. For example, 8-bromo-cyclic AMP can invoke neurite outgrowth in PC-12 cells, and magnetic fields can further simulate neurite outgrowth. The phorbol ester, TPA, can invoke neurite outgrowth, and magnetic fields can further stimulate neurite outgrowth. Moreover, PC-12D cells exposed to magnetic fields displayed enhanced neurite outgrowth, cf. Blackman et al., BEMS 14: 273–286 (1993), and this effect was enhanced as a suboptimal concentration of neurite growth factor was added to the system at the same time.

VII. Perpendicular AC/DC magnetic fields

Re-orientation of the AC/DC magnetic fields to be perpendicular to each other within the sample volume where exposure is to occur can cause radically different responses of the chemical and biological systems. In some cases the exposure situation can cause the test system to respond in the opposite direction (enhancement instead of inhibition of the biological response compared to the unexposed situation, or vice versa) as for the parallel exposure situation.

of particular importance is the use of magnetic fields described by the IPR model to enhance agents, either chemical or physical that act on or through the plasma membrane and its receptor system. The immune system is a target for the IPR method because of the variety and refined selectivity of its molecular systems for reception of information from outside the cell and for reactions that are induced at the plasma membrane level due to this stimulation. All of these are potentially subject to modification by magnetic fields as described by the IPR model.

IPR Model Applications

Although there are three apparently independent variables in the IPR model, they are coupled within the model, so that tests to demonstrate clear consistency with IPR model predictions must consider the interrelated nature of the variables. Basic tests can be used to determine whether the response observed in a particular system is consistent with the predictions of the IPR model. In each of the tests, it is critical that the magnetic fields to which the biological system is exposed are only those required by the model. Thus, it is essential that the nonparallel component of the DC magnetic field be reduced to as close to zero as possible, since no predictive model yet exists for the case of perpendicular AC and DC magnetic fields. In addition, prudent laboratory practice suggests measurement and documentation of any remaining nonparallel DC fields during testing to facilitate and clarify replication efforts between laboratories.

A. Changes in $B_{ac}$: "On Resonance"

$B_{ac}$ is the only variable unrelated to ion selection, because it appears only in the argument of the Bessel functions. Thus, a test that examines a range of $B_{ac}$ exposures while holding $B_{dc}$ and $f_{ac}$ constant provides a quick test of IPR applicability. The $f_{ac}$ and the $B_{dc}$ values should be selected so that at least one ion that is expected to be active in the system under test has a near-integer-valued frequency index. Multiple test points should be generated by varying $B_{ac}$ such that the ratio of $(n.2B_{ac}/B_{dc})$ runs from near zero (i.e., $B_{ac}=0$) to at least the first zero crossing of the least-order-selected Bessel function (i.e., the least-valued near-integer frequency index, determined by the selected values of $B_{dc}$ and $f_{ac}$). For example, if the least-order Bessel function selected is $J_1$ (n=-1), the argument range would be $n.2B_{ac}/B_{dc}$=0–3.8. The predicted system response over this range, assuming either a minimum of other near-integer frequency indices or dominance of the $J_1$ term, is approximately U-shaped. It should be noted that the value for $K_1$ (determined by the sham response for no AC field exposure) sets the starting point and the value of $K_2$ varies the depth of variation, but neither coefficient changes the relative positions of the minima, maxima, or "zero crossings" of the predicted IPR model response function. In fact, since the value of $K_1$ is set by control data, there is only one variable ($K_2$) per frequency index that can be adjusted to fit the acquired data.

B. Changes in $B_{dc}$: "Off Resonance"

Variations in the DC field strength ($B_{dc}$) change two components of the IPR model: the near-integer frequency indices and the argument of the selected Bessel functions. Since the IPR model predicts a flat response (p=constant) when no ion is at resonance, detuning for all ions through an appropriate selection of the DC flux density tests the IPR model while eliminating one of the variables in which $B_{dc}$ plays a role. Since no Bessel function is selected, there is no influence on the argument. Hydrogen provides the limiting case; its charge to mass ratio is the largest possible of all elements, and it is a potential biologically significant ion. For this "off-resonance" test, $B_{dc}$ is changed and fixed such that the frequency index for hydrogen is well below unity using the same $f_{ac}$ as the previous test. Given these fixed parameters, test points should be generated to test the system response over a range of Bessel function arguments ($n.2B_{ac}/B_{dc}$) comparable to those tested in the previous case. the predicted system response under these conditions is flat, with no variation across the range of AC field values tested.

C. Changes in $f_{ac}$

The effects observed in the preceding tests must be consistent across a variety of AC frequencies. Varying $f_{ac}$ by itself would bring different ions on and off resonance, changing their frequency indices in the process. If $B_{ac}$ and $B_{dc}$ were held constant during such tests, the results would be complicated to interpret in terms of the IPR model because a change in the frequency index for a given ion would select a different Bessel function and give it a different argument. AC learner test would examine the consistency of response when both the AC frequency and the DC flux density change proportionally to maintain the frequency indices selected in the first test. This is critical in that the effects observed in the earlier tests are specifically a function of the active ions selected. Test points should be generated to give the same argument to the Bessel functions as in the first test. In essence, this performs the first test at a different frequency. The predicted response function is the same as that predicted for the first test, e.g., U-shaped if the $J_1$ term is dominant.

Evaluation of Whole—animal Data Using the Ion Parametric Resonance Model

As noted above, the IPR model predicts specific forms of responses in biological systems induced as a result of exposure to parallel-oriented AC and DC magnetic fields. A frequency index, n, for each biologically relevant ion with charge q and mass m exposed to a given static magnetic field flux density ($B_{dc}$) and AC magnetic field frequency $f_{ac}$ is given by $n=(q/m) \cdot (B_{dc}/2\pi f_{ac})$. Resonance is defined for a given ion as any combination of $B_{dc}$ and $f_{ac}$ that produces a frequency index within 10% of an integer value. Actual resonance depends on the true bandwidth of the particular ion and is relevant only if that ion is required in the production of the observed endpoint. In most biological systems, neither of these is particularly well known. The IPR model predicts that under resonance conditions the interaction of a biologically critical ion with its biomolecular environment changes the observable response of the biological system in a predictable manner across a range of AC flux density values, $B_{ac}$, as described above. If more than one ion is at resonance, the IPR model suggests as a first approximation that the response form will be a linear sum of the response functions for all ions at resonance. When no ion which is biologically significant to the test function is at resonance, the IPR model predicts that the system's response will be unchanged across a comparable range of intensity values of Bac and is equal to the constant $K_1$.

Prato, in 1993, measured nociceptive sensitivity (i.e., latency of response to an aversive thermal surface) in snails by examining the time necessary for a snail to elevate its foot after being placed onto a warm (40±0.5° C.) surface following exposure to different values of AC magnetic fields oriented parallel to the DC magnetic fields. These tests were originally designed to test the Lednev model and tuned for $^{40}Ca^{2+}$ resonance (frequency index n=0.989) using a constant DC flux density of 78 $\mu$T (780 mg and a constant AC frequency of 690 Hz). However, the test points were selected by Prato et al. to sample only key response points predicted by the Lednev model and, therefore, provide sparse sampling of either the Lednev or the IPR model response functions.

In this test, the data presented by Prato et al. were normalized, consistent with the methods of Greene (1977) to provide a common point of reference for comparison of results between different tests. The difference in nociception levels (as measured by the mean time to lift their fully extended foot) for snails receiving inhibitor treatment but not magnetic field exposure (N) and the level for snails without inhibitor treatment or magnetic field exposure (Z) provided the range of anticipated responses in the absence of magnetic field exposure. To establish the origin of this range at zero, the value representing the nociception level for snails without inhibitor treatment or magnetic field exposure (Z) from the values measured for snails that were treated with inhibitor (S), to create the normalized data, or $$\text{Normalized data} = [S-Z]/[N-Z]$$

This data normalization does not change the form of the data, but it clearly establishes the value of $K_1$ at 1.00 to conform to the expected value for unexposed animals. Using standard statistical methods [iterative multivariate secant method (NNLIN procedure; SAS Institute, Cary, NC] to determine least squares estimates of the coefficients, the predictions of Lednev and IPR models were evaluated to determine how well the predictions accounted for variations in the experimental data. Both the residual sum of the squares and $R^2$, the multiple correlation coefficient, provide a simple, consistent characterization of the general closeness of model fit to the data. The degrees of fit ($R^2$ values) to normalized and non-normalized data are essentially identical. These results are shown in Tables 4 and 5.

TABLE 4

Normalized Nociception Level as a Function of ac Flux Density*

| Test | Exposure ($\mu$T)** | Normalized Response Time s: mean ± SE | No. of Snails | Reported Significance |
|---|---|---|---|---|
| 1 | 18 | 0.49 ± .10 | 10 | P < 0.002 |
| 2 | 40 | 0.24 ± .14 | 10 | P < 0.001 |
| 3 | 78 | 0.37 ± .11 | 10 | P < 0.001 |
| 4 | 141 | 0.19 ± .06 | 31 | P < 0.001 |
| 5 | 234 | 0.65 ± .14 | 8 | P < 0.180 |
| 6 | 297 | 0.81 ± .15 | 20 | P < 0.002 (NS) |
| 7 | 414 | 0.51 ± .12 | 10 | P < 0.003 |
| 8 | 547 | 0.71 ± .16 | 11 | P < 0.075 (NS) |

*Adapted from original data of Prato et al. [1993].
**As reported by Prato et al. [1993, 1994].

TABLE 5

Results of Different Attempts to Model Data Reported by Prato et al.*

| Case = Fitting Equation | Residual Sum of squares | $R^2$ |
|---|---|---|

Testing the $J_1$ Bessel function, assuming metric for $B_{ac}$ given in peak units

| | | |
|---|---|---|
| A1 = 1.0 − 1.12$J_1$ (Lednev) | 1.320 | 0.00 |
| A2 = 1.0 − 1.12$J_1$ (IPR) | 1.461 | 0.00 |

TABLE 5-continued

Results of Different Attempts to Model Data Reported by Prato et al.*

| Case = Fitting Equation | Residual Sum of squares | $R^2$ |
|---|---|---|
| Testing Rectification of Bessel function, metric for $B_{ac}$ given in peak units | | |
| B1 = 1.0 − $\|1.53J_1$ (Lednev)$\|$ | 0.409 | 0.00 |
| B2 = 1.0 − $\|1.53J_1$ (IPR)$\|$ | 0.675 | 0.00 |
| Testing the $J_1$ Bessel function, assuming data given in rms units (converted to peak units) | | |
| C1 = 1.0 − $\|1.53J_1$ (Lednev)$\|$ | 0.420 | 0.00 |
| C2 = 1.0. − $\|1.53J_1$ (IPR)$\|$ | 0.172 | 0.50 |
| Testing IPR model, comparing data given as peak to data given as rms and converted to peak | | |
| D1 = 1.0 − $\|$−1.50$J_1$ (pk)$\|$ | 0.674 | 0.00 |
| D2 = 1.0 − $\|$−1.75$J_1$ (rms)$\|$ | 0.117 | 0.66 |
| Testing IPR model, peak vs. rms, with more fitting equations | | |
| E1 = 1.0 − $\|$−0.48$J_1$ − 2.38$J_2$ (pk) + 2.51$J_{20}$ (pk)$\|$ | 0.316 | 0.08 |
| E2 = 1.0 − $\|$−1.81$J_1$ (rms) + 0.32$J_2$ (rms) − 1.01$J_{20}$ (rms)$\|$ | 0.088 | 0.75 |
| Testing the $J_1$ Bessel function, assuming metric for $B_{ac}$ given in peak units | | |
| F1 = 1.0 − $\|$−2.78$J_1$ (pk) − 2.16$J_2$ (pk) − 0.72$J_3$ (pk) + 2.06$J_4$ (pk) + 4.24$J_{20}$ (pk)$\|$ | 0.1243 | 0.64 |
| F2 = 1.0 − $\|$−1.79$J_1$ (rms) + 33$J_2$ (rms) − 0.96$J_3$ (rms) + 1.98$J_4$ (rms) + 2.28$J_{20}$ (rms)$\|$ | 0.0599 | 0.83 |
| Testing use of Bessel functions not selected by the IPR model, assuming data given as rms | | |
| G1 = 1.0 − $\|$−0.61$J_5$ (rms) + 7.10$J_8$ (rms)$\|$ | 0.287 | 0.16 |
| G2 = 1.0 − $\|$−3.16$J_5$ (rms) + 3.94$J_8$ (rms) − 1.43$J_7$ (rms)$\|$ | 0.169 | 0.51 |

KEY:
*Lednev = Lednev model form of argument, or (n • $B_{ac}/B_{dc}$), where n = 1 here
IPR = IPR model form of argument, or (n • $B_{ac}/B_{dc}$)

In comparing the relative degree of fit between model predictions for different assumptions of exposure metrics (i.e., exposures assumed reported as rms vs. peak), there was found initial ambiguity in exposure for the Prato data. When Prato later clarified that the exposure values reported were peak values [Prato, 194], it was expected that the analyses assuming rms values would yield more fits than analyses assuming peak values, as was the case for the Lednev model, Table 5, Case C1, as compared to case B1, with $R^2$=0.00. However, the analysis showed that the IPR model, assuming exposures given as rms and converted to peak, could account for up to 50% of the variance in the data. This was unexpected.

According to the IPR model, the resonance exposure conditions used by Prato tuned for more than just calcium ions. Candidates for biologically significant ions under the test conditions used by Prato et al. include several ions with a frequency index near 1, including calcium [40]2, cobalt 3, nickel 3, iron 3, manganese 3, two ions with an index near 2 (vanadium 5, manganese 6), one each with an index near 3 (lithium 1) and 4 (sulfur 6), and hydrogen, with a frequency index of 20. In the IPR model, when more than one ion might be involved, each ion is assumed, lacking evidence to the contrary, to function independently in producing the observed response, and the overall response is a linear, weighted sum of the individual response functions.

To examine the influence of each of these potentially significant ion categories, the Bessel functions were incrementally added to the fitting function. A steady improvement was observed in the fit of the IPR model to the data. When the remaining Bessel functions selected by the frequency index 3 and 4 ions were added to the analysis, this trend continues, as shown in Table 5, cases F1 and F2. The difference in degree of fit between models appears to be a result of the method of data collection, which provides a sparse sampling of the expected response forms.

The IPR model is useful in the following areas:

Diagnostic: by measuring the response of an ion under resonance, one may evaluate membrane surface phenomena such as receptor aggregation, involution, membrane components affecting surface molecules, and gap junction intercellular communication. Processes occurring in the nuclei of cells an also be measured, including those processes leading to DNA conformational changes and the action of gene repressors and inducers.

Cell process studies: cell differentiation, such as response to nerve growth factor, cell proliferation, and ionic components involved in cell secretion.

Cellular response to hormones such as melatonin and growth factors under magnetic field stimulation.

Alterations of chemical processes and reactions, including changes in relative dynamics of interactive metabolic networks of biochemical cycles.

Therapeutic: supplements to conventional chemotherapy in treating cancers' modulation of hormonal actions on cells.

The fact that experimental data from all test cases present herein display a response form that is consistent with the predictions of the IPR model across different values of the critical variables indicates that these molecular level interactions are fundamentally related to subsequent biological responses. The model predicts relationships between field effects on different ions and changes in an observable response such as neurite outgrowth.

It is well known that biological activity is driven by enzymatically controlled chemical reactions, and that some enzymes incorporate specific ions as cofactors to initiate or modulate their reaction rates. Further, at biologically relevant temperatures the enzyme molecules are immersed in a bath of solute molecules vibrating at infrared frequencies. Thus, it follows that ionic cofactors, their associated enzymatic reaction centers, and their dynamic interactions driven by the ever present thermal bath, are critical elements in biological activities. By "thermal," it is meant the average translations kinetic energy of molecules.

At biologically relevant temperatures, native proteins are not static forms, but fluctuate constantly, passing through a variety of similar configurations due to thermal influence. An example of a selected molecular form involves enzymes that have ligand-bound ions. These ions impart stability and conformational changes necessary to cause reaction sites to orient in ways that optimize enzymatic activity. It has been observed that different conformational states of a working protein can have the same overall structure and function, with varying structural details and rates at which the function is performed. It is assumed that the most important enzyme configurations in an active system are those that reflect the best compromise between structure with high reaction probability and small strain energy in the protein. One current approach in the study of details of ion-enzyme interactions is to use synthetic peptides to provide a more explicit description of the interaction of ions and the binding sites in proteins.

How could a change in ion energies caused by magnetic fields involve protein dynamics and lead to changes in enzyme kinetics? Thermal motions of solute molecules are relatively broadband, nonspecific influences on enzyme-ionic cofactor complexes. A critical ion may be bound in a protein cavity that shields it from collisions with solute molecules and precludes the hydration of that ion. This also supports the assumption of is unhydrated ions required by the IPR model. The natural vibration modes of the protein, particularly the ion cavity and the active site, may have evolved in tune with the vibrational modes of the specific ionic cofactor. It may be that these preferred vibratory modes for enzymatic activity are a consequence of ion cofactor binding. These modes can then be altered when the protein is bound to an ion at a predetermined site. If it is assumed that vibrational modes in enzymes contribute to their activity, then ion cofactor binding can be a major means to switch the activity on and off. Thus, the action of thermal energy from solution molecules surrounding the protein may not only promote random transitions between protein energy levels, but also supply energy to specific vibratory modes in the ion-enzyme complex that are critical for enzyme activity.

Resonant interactions of magnetic field with a bound ion can alter the vibrational dynamics between this ion and its protein ligand(s). For example, fields may alter the spatial and temporal aspects of the vibratory interaction process, the residence times at given levels, the number of levels, or the relative occupation of different levels sufficiently to distinguish the effect from random variations in these quantities. These changes could be accomplished by exceedingly small, frequency specific, amounts of energy over substantial periods of time. A change in the dynamic structure of the ionic complex could then lead to a change in the dynamic structure or the vibratory mode of the enzyme reaction site, which could ultimately lead to altered biochemical activity. This view of the dynamic interaction between proteins and ions appears to provide a critical element of possible magnetic field perturbations of these systems such as those described by the IPR model. This view of molecular vibrations may ultimately provide the link between the theoretically predicted ionic changes and the experimentally observed cell response.

The IPR model is useful for dealing with non-hydrated ions. For example, $S^{+6}$ exists only in plasma, $Ni^{+3}$ and other ions such as $Mn^{+4}$, $Cr^{+4, +5, +6}$, $V^{+4}$, etc. exist only in very specialized, high-energy ligand environments. All of these latter ions exist, outside of plasmas, in combination with oxygen or fluorine, e.g., $CrO_4^{-2}$, $VO^{+2}$, and the like. It appears that the ion response comes from a loosely-bound ion that has a low-lying "excited" state with reduced biological activity. Chemically, this is possible for metal ions such as $Mg^{+2}$ in a nitrogen environment, $Mn^{+2}$ in an oxygen environment, etc. The conformations of the enzyme and hormone must be very similar.

For example, in a protein in which $Mg^{+2}$ or $Ca^{+2}$ exists in an environment in which one donor site is supplied by a carboxamide oxygen, and the remainder of an octahedral coordination sphere comprises oxygen atoms which can move by about 1.5–2 Å. Assuming that the carboxamide proton is hydrogen bonded to some relatively electron-rich acceptor, the implication is that there exists a low-lying "excited" state in which the proton is closer to the acceptor. If a field of any sort lowers the energy of the hydrogen bonded excited state, moving the proton, on average, closer to the acceptor, the average electron density would increase on the carboxamide nitrogen. This would lower the energy of an alternate "excited" ligand field for the $Mg^{+2}/Ca^{+2}$ in which the metal is bound to the carboxamide nitrogen rather than to the carboxamide oxygen. If another field couples to the metal ion in such a way that the energy of this "excited" ligand field is lowered further, the metal ion will want to spend more time in this low-lying excited stated. However, when the metal ion moves, it exerts a force on the remainder of the ligand atoms, which leads to an altered conformation of the protein, with concomitant alteration of some or all of the activity of the protein.

Therefore, in the absence of applied field(s), there should be a low-energy infrared absorption corresponding to the sum of the hydrogen bonds plus the metal ion shift. Once this complex motion is identified, the effects of applied fields(s) can be studied.

Thus, the IPR model can be used to examine, alter and control chemical and biochemical systems, both isolated systems and systems within biological cells and organisms. The systems must contain ions which behave as hydrated ions, and the systems can be in dynamic equilibrium with the environment, i.e., living, or undergoing reactions. The systems may be undergoing regulatory control processes, as in most biological systems, and often membranes containing molecules are involved in regulatory control and signal transduction pathways. The ions are often held in ligand complexes. The most common biological systems contain hydrogen and Mg/Mn or calcium.

The effects of the IPR model can be appreciated by looking at responses of the systems alone or after treatment with other chemical or physical additives that invoke some change in the system, with and without magnetic field exposure that is tuned for specific ions of interest.

The ion binding sites are charged so as to be receptive to particular ions. In the absence of larger ions, unhydrated hydrogen or hydroxide ions are usually present as counter ions to provide neutralization of that charge. However, many reactions require larger ions as cofactors to be in some of the charged sites. For this to happen, the smaller ions, e.g., hydrogen, must be displaced. In other cases, hydrogen forms weak bonds that help stabilize the association of the larger ions, e.g., Mg, Mn, Ca, with the chemical structure, such as a protein, a nucleic acid, or a carbohydrate. In some cases, the introduction of another chemical such as a growth factor, a hormone, or a cytotoxic compound causes changes in the chemical structure that affects the interaction of the ions associated with the activity of that structure.

The IPR model defines those magnetic field exposure conditions that provide for an examination of such chemical structures as defined above to (1) determine if particular ions are involved in a reaction in such a way as to be receptive to modulation of the reaction, and (2) to alter such a reaction in ways that might enhance a desired outcome.

The novel contributions of the IPR model to the current state of the art, most particularly as defined by Liboff, are to:

(1) define a different resonance space;
(2) provide for precise description of control of the magnitude of the effect for any selected combination of parallel AC and DC magnetic fields;
(3) provide for precise description of locations of no-effect exposure results;
(4) include a requirement for hydrogen ion triggering before predicted responses for any other ions at or near resonance can create an effect;
(5) give a precise equation so that one can readily determine how to find a certain percentage of max without undue experimentation;
(6) use perpendicular magnetic fields as well as parallel magnetic fields to change ion response;
(7) describe and demonstrate what happens when there are multiple frequency-index, resonant ion responses.

In applying the IPR model, the perturbing agent is a non-resonant physical or chemical agent which causes a perturbation in the biological or chemical system, and the resonant electromagnetic fields condition causes a change in that perturbation, the magnitude of which can be controlled by the IPR model calculations for $B_{ac}$ flux density.

The IPR model can be used to control ions at whatever level is required, and that the proper exposure conditions can be localized within an entity, such as a human. The magnetic fields can be focused in an area to control the effect over a selected spatial area. The IPR provides a precise description of the control of the magnitude of the effect, and affords a precise description to the locations of no-effect exposure results. The predicted effect for hydrogen ions must be significantly different from zero before the effect predicted for other ions, including those at n=1, can be seen. Multiple frequency index resonant ion responses can be considered.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references and patents cited herein are hereby incorporated in their entirety.

REFERENCES:

Abrams, M. J., Murrer B. A. (1993): "Metal Compounds in Therapy and Diagnosis". *Science* 261: 725–730.

Adair, R. K. (1991): "Constraints on Biological Effects of Weak Extremely-Low-Frequency Electromagnetic Fields". *Physical Review A* 43: 1039–1048.

Adair, R. K. (1992): "Criticism of Lednev's Mechanism for the Influence of Weak Magnetic Fields on Biological Systems." *Biolelectromagnetics* 13: 231–235.

Adey, W. R. (1992): "Collective Properties of Cell Membranes". In Norden, B., Ramel C. (eds): *Interaction Mechanisms of Low-Level Electroma gnetic Fields in Living Systems*. Oxford: Oxford University Press, pp: 47–77.

Bialek, W., Bruno W. J., Joseph, J., Onuchic J. N. (1989): "Quantum and Classical Dynamics in Biochemical Reactions". *Photosynthesis Research* 22: 15–27.

Bianco, B., Chiabrera, A. (1992): "From the Langevin-Lorentz to the Zeeman Model of Electromagnetic Effects on Ligand-Receptor Binding". *Bioelectrochemistry and Bioenergetics* 28: 355–365.

Blackman, C. F., Blanchard, J. P., Benane, S. G., House, D. E. (1995): "The Ion Parametric Resonance Model Predicts Magnetic Field Parameters that Affect Nerve Cells". *FASEB J* 9: 547–551.

Blackman, C. F., Blanchard, J. P., Benane, S. G., House, D. E. (1994): "Empirical Test of an Ion Parametric Resonance Model for Magnetic Field Interactions with PC-12 Cells". *Bioelectromagnetics* 15: 239–260.

Blackman, C. F. (1992): "Calcium Release from Neural Tissue: Experimental Results and Possible Mechanisms". In Norden, B., Ramel, C., (eds): *Interaction Mechanisms of Low-Level Electromagnetic Fields in Living Systems*. Oxford: Oxford University Press, pp. 107–129.

Blackman, C. F., Benane, S. G., Rabinowitz, J. R., House, D. E., Joines, W. T. (1985): "A Role for the Magnetic Field in the Radiation-Induced Efflux of Calcium Ions from Brain Tissue, in vitro". *Bioelectromagnetics* 6: 327–337.

Blackman, C. F., Benane, S. G., Elliott, D. J., House, D. E., Pollock, M. M. (1988): "Influence of Electromagnetic Fields on the Efflux of Calcium Ions from Brain Tissue in vitro: A Three-Model Analysis Consistent with the Frequency Response up to 510 Hz". *Bioelectromagnetics* 9(3): 215–227.

Blackman, C. F., Benane, S. G., House, D. E., Elliott, D. J. (1990): "Importance of Alignment Between Local DC Magnetic Field and an Oscillating Magnetic Field in Responses of Brain Tissue in vitro and in vivo". *Bioelectromagnetics* 11(2): 159–167.

Blackman, C. F., Benane, S. G., House, D. E., (1993): "Evidence for Direct Effect of Magnetic Fields on Neurite Outgrowth". *FASEB J* 7: 801–806.

Blackman, C. F., Beneane, S. G., Kinney, L. S., Joines, W. T., House, D. E. (1982): "Effects of ELF Fields on Calcium-Ion Efflux from Brain Tissue in vitro". *Radiation Research* 92: 510–520.

Blackman, C. F., Kinney, L. S., House, D. E., Joines, W. T. (1989): "Multiple Power-Density Windows and Their Possible Origin". *Bioelectromagnetics* 10(2): 115–128.

Blackman, C. F., Benane, S. G., House, D. E. (1995b): "Frequency-Dependent Interference by Magnetic Fields of Nerve-Growth-Factor-induced Neurite Outgrowth in PC-12 Cells". *Bioelectromagnetics,* accepted for publication.

Blanchard, J. P., Blackman, C. F., (1994): "Clarification and Application of an Ion Parametric Resonance Model for Magnetic Field Interactions with Biological Systems". *Bioelectromagnetics* 15: 217–238.

Blanchard, J. P., House, D. E., Blackman, C. F. (1994a): "Evaluation of Whole Animal Data Using the Ion Parametric Resonance Model". *Bioelectromagnetics*, accepted for publication.

Blanchard, J. P., Blackman, C. F. (1994b): "A Model of Magnetic Field Effects on Biological Systems with Confirming Data from a Cell Culture Preparation". In Frey, A. H. (ed): *On the Nature of Electromagnetic Field Interactions with Biological Systems.* R. G. Landes: USA, 1994, pp. 43–58.

Blanchard, J. P., Blackman, C. F., Beneane, S. G., House, D. E. (1994c): "Resonance Bandwidth Under IPR Model Exposure Conditions". The 1994 Annual Review of Research on Biological Effects of Electric and Magnetic Fields from the Generation, Delivery and Use of Electricity, Nov. 6–10, 1994, Albuquerque, N.Mex.

Chiabrera, A., Bianco, B. (1991): "Quantum Dynamics of Ions in Molecular Crevices Under Electromagnetic Exposure". "In Brighton, C. T. Pollack, S. R. (eds)" *Electromagnetics in Biology and Medicine.* San Francisco: San Francisco Press, pp. 21–26.

Chiabrera, A., Bianco, B., Kauffman, J. J., Pilla, A. A. (1991): "Quantum Analysis of Ion Binding Kinetics in Electro-magnetic Bioeffects". In Brighton, C. T., Pollack, S. R. (eds): *Electromagnetics in Biology and Medicine.* San Francsico: San Francisco Press, pp. 27–31.

Chiabrera, A., Bianco, B., Moggia, E. (1993): "Effect of Lifetimes on Ligand Binding Modelled by the Density Operation."*Bioelectrochemistry and Bioenergetics* 30: 35–42.

Durney, C. H., Rushforth, C. K., Anderson, A. A. (1988): "Resonant DC-AC Magnetic Fields: Calculated Response". *Bioelectromagnetics* 9(4): 315–336.

Edmonds, D. T. (1993): "Larmor Precession as a Mechanism for the Detection of Static and Alternating Magnetic Fields". *Bioelectrochemistry and Bioenergetics* 30: 3–12.

EPRI (1990): "The Cyclotron Resonance Hypothesis: An EMF Health Effects Resource Paper", Electric Power Research Institute, Palo Alto, Calif., EN.3014.3.90.

Frauenfelder, H., Parak, F., Young, R. D. (1988); "Conformational Substrates in Proteins" *Ann. Rev. Biophys. Biophys. Chem.* 17: 451–479.

Greene, L. A. (1977): "A Quantitative Bioassay for Nerve Growth Factor (NGF) Activity Employing a Clonal Pheochromo-cytoma Cell Line". *Brain Research* 133: 350–353.

Greene, L. A. and Tischler, A. S. (1976): "Establishment of a Noradrenergic Clonal Line of Rat Adrenal Pheochromocytoma Cells Which Respond to Nerve Growth Factor". *Proc. Nat. Acad. Sci.* (USA) 73: 2424–2428.

Halle, B. (1988): "On the Cyclotron Resonance Mechanism for Magnetic Field Effects on Transmembrane Ion Conductivity". *Bioelectromagnetics* 9: 381–385.

Karlin, K. D., (1993): "Metalloenzymes, Structural Motifs, and Inorganic Models". *Science* 261: 701–708.

Karplus, M., Brunger, A. T., Elber, R., Kuriyan, J. (1987): "Molecular Dynamics: Applications to Proteins". *Cold Siring Harbor Symposia on Ouantitative Biology*, Vol. LII, Cold Spring Harbor Laboratory, 381–390.

Karplus, M., Petsko, G. A. (1990): "Molecular Dynamics Simulations in Biology". *Nature* 347: 631–639.

Landreth, G. E., Smith, D. S., McCabe, D., Gittinger, C. (1990): "Characterization of a Nerve Growth Factor-Stimulated Protein Kinase in PC-12 Cells Which Phosphorylates Microtubule-Associated Protein 2 and pp250". *J. Neurochem.* 55: 514–523.

Lednev, V. V. (1991): "Possible Mechanism for the Influence of Weak Magnetic Fields on Biological Systems". *Bioelectromagnetics* 12: 71–75.

Lerchl, A., Reiter, R. J., Howes, K. A., Nonaka, K. O., Stokkan, K-A. (1991): "Evidence that Extremely Low Frequency $Ca^{2+}$) -Cyclotron Resonance Depresses Pineal Melatonin Synthesis in View". *Neuroscience Letters* 124: 213–215.

Levi, A., Biocca, S., Cattaneo, A., Calissano, P. (1988): "The Mode of Action of Nerve Grwoth Factor in PC-12 Cells". *Molecular Neurobioloqy* 2: 201–226.

Liboff, A. R. (1985): "Cyclotron Resonance in Membrane Transport". In Chiabrera, A., Nicolini, C., Schwan, H. P. (eds): "Interactions Between Electromagnetic Fields and Cells". *NATO ASI* Series A 97. New York: Plenum, pp. 281–296.

Liboff, A. R., Smith, S. D., McLeod, B. R. (1987): "Experimental Evidence for Ion Cyclotron Resonance Mediation of Membrane Transport". In Blank, M., Findl, E. (eds): *Mechanistic Approaches to Interactions of Electric and Electromagnetic Fields with Living Systems.* New York: Plenum, pp. 109–132.

Liboff, A. R., Parkinson, W. C. (1991): "Search for Ion-Cyclotron Resonance in an Na+-Transport System. *Bioelectromagnetics* 12: 77–84.

Liboff, A. R. (1992): "The Cyclotron Resonance' Hypothesis: Experimental Evidence and Theoretical Constraints". In Norden, B., Ramel, C. (eds): *Interaction Mechanisms of Low-Level Electromagnetic Fields and Living Systems.* Oxford: Oxford University Press, pp. 130–147.

Liburdy, R. P., Sloma, T. R., Sokolic, R., Yaswen, P. (1993): "ELF Magnetic Fields, Breast Cancer, and Melatonin: 60 Hz Fields Block Melatonin's Oncostatic Action on ER+Breast Cancer Cell Proliferation". *J. Pineal Res.* 14: 89–97.

Lippard, S. J. (1993): "Bioinorganic Chemistry: A Maturing Frontier". *Science* 261: 699–700.

McLeod, B. R., Liboff, A. R. (1987): "Cyclotron Resonance in Cell Membranes; the Theory of the Mechanism". In Blank, M., Findl, E. (eds): *Mechanistic Approaches to Interactions of Electric and Electromagnetic Fields with Living Systems.* New York: Plenum, pp. 97–108. O'Halloran, T.V. (1993): "Transition Metals in Control of Gene Expression". *Science* 261: 715–725.

Podgoretskii, M. I., Khrustalev, O. A. (1964): "Interference Effects in Quantum Transitions". *Soviet Physics Uspekhi* 6(5): 682–700.

Pyle, A. M. (1993): "Ribozymes: A Distinct Class of Metallo-enzymes". *Science* 261: 709–714.

Regan, L. (1993): "The design of Metal-Binding Sites in Proteins". In Engelman, D. M., Cantor, C. R., Pollard, T. D. (eds): *Annual Review of Biophysics and Biomolecular Structure.* Palo Alto: Annual Reviews, Inc. pp.257–281.

Ross, S. M. (1990): Combined DC and ELF Magnetic Fields can Alter Cell Proliferation". *Bioelectromagnetics* 11: 27–36.

Rukenstein, A., Greene, L. A. (1983): "The Quantitative Bioassay of Nerve Growth Factor: Use of Frozen Primed' PC-12 Pheochromocytoma Cells". *Brain Research* 263: 177–180.

Sandweiss, J. (1990): "On the Cyclotron Resonance Model of Ion Transport". *Bioelectromagnetics* 11: 203–205.

Sandyk, R. (1993): "Weak Magnetic Fields Antagonize the Effects of Melatonin on Blood Glucose Levels in Parkinson's Disease". *Intern. J. Neuroscience* 68: 85–91.

Sano, M. (1992): "Chromatographic Resolution and Characterization of a Nerve Growth Factor–Dependent Kinase that Phosphorylates Microtubule-Associated Proteins 1 and 2 in PC-12 Cells". *J. Neurochem.* 59: 1263–1272.

Smith, S. D., McLeod, B. R., Liboff, A. R., Cooksey, K. (1987): "Calcium Cyclotron Resonance and Diatom Mobility". *Bioelectromagnetics* 8(3): 215–227.

Thomas, J. R., Schrot, J., Liboff, A. R. (1986): "Low-Intensity Magnetic Fields Alter Operant Behavior in Rats". *Bioelectromagnetics* 7: 349–357.

Trillo, A., Ubeda, A. Blanchard, J. P., House, D. E., Blackman, C. F. (1994): "Effects of AC/DC Magnetic Fields Under Resonant Conditions for the Hydrogen Ion on the NGF-Induced Neurite Outgrowth in PC-12 Cells". Abstract accepted for presentation at the 16th Annual Meeting of the Bioelectromagnetics Society, Copenhagen, Denmark, Jun. 12–17 1994.

Ubeda, A., Trillo, M. A., House, D. E., Blackman, C. F. (1995): "Melatonin Enhances Junctional Transfer in Normal C3H/10T1/2 Cells". *Cancer Letters,* in press.

Ubeda, A., Trillo, M. A., House, D. E., Blackman, C. F. (1995): "A 50-Hz Magnetic Field Blocks Melatonin-Induced Enhancement of Junctional Transfer in Normal C3H/10T1/2 Cells". Submitted to *Carcinogenisis.*

Yariv, A. (1982): *An Introduction to Theory and Applications of Quantum Mechanics.* John Wiley and Sons, Inc., New York, pp. 232–233.

What is claimed is:

1. A method for acting on a system in a process selected from the group consisting of examining, altering, and controlling said system and combinations thereof, said method comprising acting on a biological or chemical system containing at least one entity with a charge to mass ratio of an unhydrated ion which responds to imposition of a magnetic field when said system contains at least one entity with a charge to mass ratio of an unhydrated ion is exposed to AC and DC magnetic fields comprising:

selecting at least one entity with a charge to mass ratio of an unhydrated ion to be stimulated within said system;

exposing said system to parallel AC and DC magnetic fields to create a response for said at least one entity, wherein the AC frequency, $f_{ac}$, and the DC magnitude, $B_{dc}$, are set so that the value of n is an integer to create a resonance for said at least one entity;

wherein, $n = (q/m)B_{dc}/2\pi f_{ac}$; and varying the magnitude of the AC field, $B_{ac}$, wherein the degree of response of said system to an imposed magnetic field is calculated as p, wherein $p = K_1 + K_2(-1)^n J_n(n2B_{ac}/B_{dc})$;

wherein $J_n$ is a Bessel function of the first order n, selected by the integer valued frequency index n, where q is the charge of the entity, m is the mass of the entity, $B_{dc}$ is the magnitude of the DC magnetic field and $f_{ac}$ is the frequency of the AC magnetic field, $B_{ac}$ is the peak AC flux density, $K_1$ is the response of the system when $B_{ac}=0$ and $K_2$, which calibrates the predicted response of the measurement system applied to a chemical or biological system is determined by exposing the chemical or biological system to a peak valued AC flux density selected such that $J_n$ ($2nB_{ac}/B_{dc}$) is not zero, where $K_2$ is $(p-K_1)/J_n$ ($2nB_{ac}/B_{dc}$) except where n=1 and Bac=Bdc.

2. The method according to claim 1 wherein $K_2$ is established by up to three tests at values of $2nB_{ac}/B_{dc}=1.4$, 1.8 and 2.3, which then calibrates all subsequent predicted responses.

3. The method according to claim 1 comprising:
   a. after selecting the at least one entity to be stimulated within said system;
   b. observing said chemical or biological system over a predetermined period of time without externally perturbing said chemical or biological system;
   c. treating said chemical or biological system with at least one agent;
   d. exposing said chemical or biological system to a combination of parallel AC and DC magnetic fields to create a resonance for said at least one entity and defining resonance as an integer valued frequency index, n;
   e. observing said chemical or biological system over a predetermined period of time;
   f. comparing the responses of said chemical or biological system to said combination of AC and DC magnetic fields before and after the chemical or biological system has been treated with said at least one agent; and
   g. determining the degree of response of said at least one entity to said imposed magnetic field as p.

4. The method according to claim 3 wherein said at least one agent is selected from the group consisting of natural hormones, synthetic hormones, growth factors, chemotherapeutic compounds, and cytotoxic compounds.

5. The method according to claim 3 wherein said at least one agent is selected from the group consisting of melatonin, tamoxifen, pertussis toxin, chloral hydrate, adriamycin, cytosine arabinoside, and nerve growth factor.

6. The method according to claim 1 wherein the at least one entity which responds when exposed to AC and DC magnetic fields is hydrogen and the AC frequency, $f_{ac}$, and the DC flux density, $B_{dc}$, are selected such that the ratio $B_{dc}/f_{ac}$ is an integer multiple of 0.66, and the integer by which said ratio is a multiple selects the order of the Bessel function.

7. The method according to claim 1 wherein at least two entities which have charge to mass ratios of unhydrated ions which respond to imposition of a magnetic field are present and, when said at least two entities have different frequency indices, the $K_2$ for each of said at least two entities differs for each entity, and the predicted response form for the system is the sum of the frequency response form for each of the frequency indices.

8. The method according to claim 7 wherein one of said at least two entities is hydrogen and the response of hydrogen ion dominates the response of the chemical or biological system until $B_{ac}$ is sufficiently large to overcome the response of the hydrogen ion.

9. The method according to claim 3 wherein the at least one entity which responds when exposed to AC and DC magnetic fields is hydrogen and the AC frequency, $f_{ac}$, and the DC flux density, $B_{dc}$, are selected such that the ratio $B_{dc}/f_{ac}$ is an integer multiple of 0.66, and the integer by which said ratio is a multiple selects the order of the Bessel function.

10. The method according to claim 3 wherein at least two entities which have charge to mass ratios of unhydrated ions which respond to imposition of a magnetic field are present and, when said at least two entities have different frequency indices, the $K_2$ for each of said at least two entities differs for each entity, and the predicted response form for the system is the sum of the frequency response form for each of the frequency indices.

11. The method according to claim 10 wherein one of said at least two entities is hydrogen and the response of hydrogen ion dominates the response of the chemical or biological system until $B_{ac}$ is sufficiently large to overcome the response of the hydrogen ion.

12. The method according to claim 1 for affecting the action of a chemical or biological system which contains at least one entity which has a charge to mass ratio of an unhydrated ion which responds to imposition of a magnetic field comprising:

applying to said system containing at least one entity a combination of parallel AC and DC magnetic fields wherein the AC frequency, $f_{ac}$, and the DC magnitude, $B_{dc}$, are selected such that the ratio $f_{ac}/B_{dc}$ is used to control the amount of affect imparted to the system.

13. The method according to claim 1 for affecting the action of a chemical or biological system which contains at least one entity which has a charge to mass ratio of an unhydrated ion which responds to imposition of a magnetic field comprising:

applying to said system containing at least one entity a combination of parallel AC and DC magnetic fields wherein the AC frequency, $f_{ac}$, and the DC magnitude, $B_{dc}$, are selected such that the ratio $f_{ac}/B_{dc}$ is used to control the amount of affect imparted to the system;

and wherein said AC and DC magnetic fields are off-resonance parallel to each other.

* * * * *